United States Patent
Wang et al.

(10) Patent No.: US 7,560,464 B2
(45) Date of Patent: Jul. 14, 2009

(54) POLYCYCLIC PYRIMIDINES AS POTASSIUM ION CHANNEL MODULATORS

(75) Inventors: Xiaodong Wang, Chapel Hill, NC (US); Kerry Leigh Spear, Cambridge, MA (US); Alan Bradley Fulp, Willow Spring, NC (US); Darrick Seconi, Cary, NC (US); Takeshi Suzuki, Ibaraki (JP); Takahiro Ishii, Ibaraki (JP); Ayako Moritomo, Ibaraki (JP)

(73) Assignee: Icagen, Inc., Durham, NC (US)

( * ) Notice: Subject to any disclaimer, the term of this patent is extended or adjusted under 35 U.S.C. 154(b) by 430 days.

(21) Appl. No.: 11/105,938

(22) Filed: Apr. 13, 2005

(65) Prior Publication Data

US 2005/0267089 A1   Dec. 1, 2005

Related U.S. Application Data

(60) Provisional application No. 60/561,990, filed on Apr. 13, 2004.

(51) Int. Cl.
| C07D 401/14 | (2006.01) |
| A61K 31/444 | (2006.01) |
| A61P 25/08 | (2006.01) |
| A61P 25/16 | (2006.01) |
| A61P 25/24 | (2006.01) |
| A61P 25/28 | (2006.01) |

(52) U.S. Cl. ............... 514/256; 514/269; 514/272; 514/275; 544/316; 544/323; 544/324

(58) Field of Classification Search ............ 544/316, 544/323, 324; 514/256, 269, 272, 275
See application file for complete search history.

(56) References Cited

U.S. PATENT DOCUMENTS

| 5,863,924 A | 1/1999 | Berger et al. |
| 5,952,331 A | 9/1999 | Berger et al. |
| 5,958,934 A | 9/1999 | Berger et al. |

FOREIGN PATENT DOCUMENTS

| DE | 1271116 B | 6/1968 |
| EP | 0431421 A2 | 6/1991 |
| WO | WO95/19358 A1 | 7/1995 |
| WO | WO00/39101 A1 | 7/2000 |
| WO | WO00/51987 A2 | 9/2000 |
| WO | WO00/78731 A1 | 12/2000 |
| WO | WO02/47690 A1 | 6/2002 |
| WO | WO02/006606 A1 | 8/2002 |
| WO | WO03/027100 A1 | 4/2003 |
| WO | WO03/077656 A1 | 9/2003 |
| WO | WO03/094861 A2 | 11/2003 |
| WO | WO2004/039934 A1 | 5/2004 |
| WO | WO2004/065378 A1 | 8/2004 |

OTHER PUBLICATIONS

Cleary et al., Br. J. Opthalmol., 89, 223-228, 2005.*
Jenkinson, DH., Br. J. Pharmacol., 147 Suppl. 1, S63-71, 2006.*
Spickett, R.G.W., et al. Quaternary Salts from 2-Chloro-5-nitropyrimidines. Part 1. Preparation and Some Reactions', *Journal of the Chemical Society. Abstracts* (1955) XX:4354-4359.

* cited by examiner

*Primary Examiner*—Venkataraman Balasubramanian
(74) *Attorney, Agent, or Firm*—Townsend and Townsend and Crew LLP

(57) ABSTRACT

The present invention provides a genus of polycyclic pyrimidines that are useful as modulators of potassium ion channels. The modulators of the invention are of use in both therapeutic and diagnostic methods.

15 Claims, No Drawings

POLYCYCLIC PYRIMIDINES AS POTASSIUM ION CHANNEL MODULATORS

CROSS-REFERENCES TO RELATED APPLICATIONS

This application claims the benefit of U.S. Provisional Patent Application No. 60/561,990, filed Apr. 13, 2004, which is incorporated herein by reference in its entirety for all purposes.

BACKGROUND OF THE INVENTION

Ion channels are cellular proteins that regulate the flow of ions, including calcium, potassium, sodium and chloride into and out of cells. These channels are present in all human cells and affect such physiological processes as nerve transmission, muscle contraction, cellular secretion, regulation of heartbeat, dilation of arteries, release of insulin, and regulation of renal electrolyte transport. Among the ion channels, potassium ion channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium ion channels are typically formed by four alpha subunits, and can be homomeric (made of identical alpha subunits) or heteromeric (made of two or more distinct types of alpha subunits). In addition, certain potassium ion channels (those made from Kv, KQT and Slo or BK subunits) have often been found to contain additional, structurally distinct auxiliary, or beta subunits. These subunits do not form potassium ion channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493: 625-633 (1996); Shi et al., *Neuron* 16(4): 843-852 (1996)). In another example, the KQT family beta subunit, minK, primarily changes activation kinetics (Sanguinetti et al., *Nature* 384: 80-83 (1996)).

The alpha subunits of potassium ion channels fall into at least 8 families, based on predicted structural and functional similarities (Wei et al., *Neuropharmacology* 35(7): 805-829 (1997)). Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. Small (SK) and intermediate (IK) conductance calcium-activated potassium ion channels possess unit conductances of 2-20 and 20-85 pS, respectively, and are more sensitive to calcium than are BK channels discussed below. For a review of calcium-activated potassium channels see Latorre et al., *Ann. Rev. Phys.* 51: 385-399 (1989).

Three other families of potassium channel alpha subunits have distinct patterns of transmembrane domains. Slo or BK family potassium channels have seven transmembrane domains (Meera et al., *Proc. Natl. Acad. Sci. U.S.A.* 94(25): 14066-14071 (1997)) and are gated by both voltage and calcium or pH (Schreiber et al., *J. Biol. Chem.* 273: 3509-3516 (1998)). Slo or BK potassium ion channels are large conductance potassium ion channels found in a wide variety of tissues, both in the central nervous system and periphery. These channels are gated by the concerted actions of internal calcium ions and membrane potential, and have a unit conductance between 100 and 220 pS. They play a key role in the regulation of processes such as neuronal integration, muscular contraction and hormone secretion. They may also be involved in processes such as lymphocyte differentiation and cell proliferation, spermatocyte differentiation and sperm motility. Members of the BK (Atkinson et al., *Science* 253: 551-555 (1991); Adelman et al., *Neuron* 9: 209-216 (1992); Butler, *Science* 261: 221-224 (1993)) subfamily have been cloned and expressed in heterologous cell types where they recapitulate the fundamental properties of their native counterparts. Finally, the inward rectifier potassium channels (Kir), belong to a structural family containing two transmembrane domains, and an eighth functionally diverse family (TP, or "two-pore") contains two tandem repeats of this inward rectifier motif.

Each type of potassium ion channel shows a distinct pharmacological profile. These classes are widely expressed, and their activity hyperpolarizes the membrane potential. Potassium ion channels have been associated with a number of physiological processes, including regulation of heartbeat, dilation of arteries, release of insulin, excitability of nerve cells, and regulation of renal electrolyte transport. Moreover, studies have indicated that potassium ion channels are a therapeutic target in the treatment of a number of diseases including central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as targets for neuroprotective agents (e.g., to prevent stroke and the like); as well as disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomia, diabetes type II, hyperinsulinemia, premature labor, baldness, cancer, and immune suppression.

Specifically, SK channels have been shown to have distinct pharmacological profiles. For example, using patch clamp techniques, the effects of eight clinically relevant psychoactive compounds on SK2 subtype channels were investigated (Dreixler et al., *Eur. J. Pharmacol.* 401: 1-7 (2000)). The evaluated compounds are structurally related to tricyclic antidepressants and include amitriptyline, carbamazepine, chlorpromazine, cyproheptadine, imipramine, tacrine and trifluperazine. Each of the compounds tested was found to block SK2 channel currents with micromolar affinity. A number of neuromuscular inhibiting agents exist that affect SK channels, e.g. apamin, atracurium, pancuronium and tubocurarine (Shah et al., *Br J Pharmacol* 129: 627-30 (2000)).

Moreover, patch clamp techniques have also been used to study the effect of the centrally acting muscle relaxant chlorzoxazone and three structurally related compounds, 1-ethyl-2-benzimidazolinone (1-EBIO), zoxazolamine, and 1,3-dihydro- 1-[2-hydroxy-5-(trifluoromethyl)phenyl]-5-(trifluoromethyl)-2H-benzimidazol-2-one (NS 1619) on recombinant rat brain SK2 channels (rSK2 channels) expressed in HEK293 mammalian cells (Cao et al., *J Pharmacol. Exp. Ther.* 296: 683-689 (2001)). When applied externally, chlorzoxazone, 1-EBIO, and zoxazolamine activated rSK2 channel currents in cells dialyzed with a nominally calcium-free intracellular solution.

The effects of metal cations on the activation of recombinant human SK4 (also known as hIK1 or hKCa4) channels has also been studied (Cao and Houamed, *FEBS Lett.* 446: 137-41 (1999)). The ion channels were expressed in HEK 293 cells and tested using patch clamp recording. Of the nine metals tested, cobalt, iron, magnesium, and zinc did not activate the SK4 channels when applied to the inside of SK4 channel-expressing membrane patches. Barium, cadmium, calcium, lead, and strontium activated SK4 channels in a concentration-dependent manner. Calcium was the most potent metal, followed by lead, cadmium, strontium, and barium.

The SK channels are heteromeric complexes that comprise pore-forming α-subunits and the calcium binding protein calmodulin (CaM). CaM binds to the SK channel through the CaM-binding domain (CaMBD), which is located in an intracellular region of an α-subunit close to the pore. Based on a recently published crystal structure, calcium binding to the N-lobe of the CaM proteins on each of the four subunits initiates a structural change that allows a hydrophobic portion of the CaM protein to interact with a CaMBD on an adjacent subunit. As each N-lobe on an adjacent subunit grabs the other CaMBD C-terminal region, a rotary force is thought to be created between them which would drive open the channel.

New classes of compounds that act to modulate the opening of potassium ion channels would represent a significant advance in the art and provide the opportunity to develop treatment modalities for numerous diseases associated with these channels. The present invention provides a new class of potassium ion channel modulators and methods of using the modulators.

BRIEF SUMMARY OF THE INVENTION

The present invention provides polycyclic pyrimidines, prodrugs, complexes, and pharmaceutically acceptable salts thereof, which are useful in the treatment of diseases through the modulation of potassium ion flow through potassium ion channels.

In a first aspect, the potassium ion channel modulator is a compound according to Formula I:

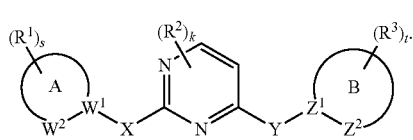

(I)

In Formula (I), A and B are independently substituted or unsubstituted 5- or 6-membered heterocycloalkyl or substituted or unsubstituted 5- or 6-membered heteroaryl. The symbol $W^1$ is —C= or —N—.

$W^2$ is —CH=, —NH—, —N=, or —O—.

The symbol $Z^1$ is —C=, —N—, or —$\overset{\oplus}{N}$—.

$Z^2$ is —CH=, —NH—, —N=, or —O—.

The symbol X is a bond, —CH$_2$—, or —NR$^4$—. Y is a bond, —CH=N—NH—, —NH—CH$_2$—, or —NR$^5$—.

The symbols s and t are independently integers from 1 to 4.

The symbol k is an integer from 1 to 2.

$R^1$, $R^2$, and $R^3$ are independently H, —OH, —NH$_2$, —NO$_2$, —SO$_2$NH$_2$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, substituted or unsubstituted heteroaryl, or —NR$^7$R$^8$.

$R^7$ and $R^8$ are independently H, halogen, substituted or unsubstituted alkyl, substituted or unsubstituted heteroalkyl, substituted or unsubstituted 5- to 7-membered cycloalkyl, substituted or unsubstituted 5- to 7-membered heterocycloalkyl, substituted or unsubstituted aryl, or substituted or unsubstituted heteroaryl. $R^7$ and $R^8$ are optionally joined together with the nitrogen to which they are attached to form a substituted or unsubstituted 5- to 7-membered heterocycloalkyl, or substituted or unsubstituted heteroaryl.

$R^4$ and $R^5$ are independently H, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, or substituted or unsubstituted heteroaryl.

Where a plurality of $R^1$, $R^2$, and/or $R^3$ groups are present, each $R^1$, $R^2$, and/or $R^3$ is optionally different.

$R^1$, $R^2$, and $R^3$ may optionally form part of a fused ring system.

In a second aspect, the present invention provides a method for decreasing ion flow through potassium ion channels in a cell, comprising contacting the cell with a potassium ion channel modulating amount of a modulator of the present invention.

In a third aspect, the present invention provides a method for treating a disease through the modulation of potassium ion flow through potassium ion channels. The modulators are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), and as neuroprotective agents (e.g., to prevent stroke and the like). The modulators of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression. This method involves administering, to a patient, an effective amount of a modulator of the present invention.

In a fourth aspect, the present invention provides a pharmaceutical composition comprising a pharmaceutically acceptable carrier and a modulator of the present invention.

These and other aspects and embodiments of the invention will be apparent from the detailed description that follows.

DETAILED DESCRIPTION OF THE INVENTION

I. Abbreviations and Definitions

The abbreviations used herein have their conventional meaning within the chemical and biological arts.

Where moieties are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ or 1- to 10-membered means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—C(=O)—$CH_3$, —$CH_2$—$CH_2$—$CH_2$—C(=O)—O—C($CH_3$)—$CH_3$, —$CH_2$—$CH_2$—$CH_2$—C(=O)—N—CH($CH_3$), —$CH_2$—$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated and unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridinyl, 3-pyridinyl, 4-pyridinyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O) NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1 to 3 halogens, substituted or unsubstituted alkyl, alkoxy or thioalkoxy groups, or arylalkyl groups. When a modulator of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R''', —OC (O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system;

and where R', R", R''' and R'''' are preferably independently selected from hydrogen, alkyl, heteroalkyl, aryl and heteroaryl. When a modulator of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" is meant to include oxygen (O), nitrogen (N), sulfur (S) and silicon (Si).

A "substituent group," as used herein, means a group selected from the following moieties:

(A) —OH, —NH$_2$, —SH, —CN, —CF$_3$, oxy, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2- to 20-membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active modulators which are prepared with relatively nontoxic acids or bases, depending on the particular substituents found on the modulators described herein. When modulators of the present invention contain relatively acidic functionalities, base addition salts can be obtained by contacting the neutral form of such modulators with a sufficient amount of the desired base, either neat or in a suitable inert solvent. Examples of pharmaceutically acceptable base addition salts include sodium, potassium, calcium, ammonium, organic amino, or magnesium salt, or a similar salt. When modulators of the present invention contain relatively basic functionalities, acid addition salts can be obtained by contacting the neutral form of such modulators with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science* 66: 1-19 (1977)). Certain specific modulators of the present invention contain both basic and acidic functionalities that allow the modulators to be converted into either base or acid addition salts.

The neutral forms of the modulators are preferably regenerated by contacting the salt with a base or acid and isolating the parent modulator in the conventional manner. The parent form of the modulator differs from the various salt forms in certain physical properties, such as solubility in polar solvents.

In addition to salt forms, the present invention provides modulators, which are in a prodrug form. Prodrugs of the modulators described herein are those compounds or complexes that readily undergo chemical changes under physiological conditions to provide the modulators of the present invention. Additionally, prodrugs can be converted to the modulators of the present invention by chemical or biochemical methods in an ex vivo environment. For example, prodrugs can be slowly converted to the modulators of the present invention when placed in a transdermal patch reservoir with a suitable enzyme or chemical reagent.

The term "ring" as used herein means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring are typically defined by the number of members in the ring. For example, a "5- to 7-membered ring" means there are 5-7 atoms in the encircling arrangement. The ring optionally includes a heteroatom. Thus, the term "5- to 7-membered ring" includes, for example pyridinyl, piperidinyl and thiazolyl rings.

The term "poly" as used herein means at least 2. For example, a polyvalent metal ion is a metal ion having a valency of at least 2.

"Moiety" refers to the radical of a molecule that is attached to another moiety.

The symbol ∿, whether utilized as a bond or displayed perpendicular to a bond indicates the point at which the displayed moiety is attached to the remainder of the molecule.

Certain modulators of the present invention can exist in unsolvated forms as well as solvated forms, including hydrated forms. In general, the solvated forms are equivalent to unsolvated forms and are encompassed within the scope of the present invention. Certain modulators of the present invention may exist in multiple crystalline or amorphous forms. In general, all physical forms are equivalent for the uses contemplated by the present invention and are intended to be within the scope of the present invention.

Certain modulators of the present invention possess asymmetric carbon atoms (optical centers) or double bonds; the racemates, diastereomers, geometric isomers and individual isomers are encompassed within the scope of the present invention.

The modulators of the present invention may also contain unnatural proportions of atomic isotopes at one or more of the atoms that constitute such modulators. For example, the modulators may be radiolabeled with radioactive isotopes, such as for example tritium ($^3$H), iodine-125 ($^{125}$I) or carbon-14 ($^{14}$C). All isotopic variations of the modulators of the present invention, whether radioactive or not, are encompassed within the scope of the present invention.

II. Potassium Ion Channel Modulators

The invention provides potassium ion channel modulators that include a pyrimidinyl moiety and a first and a second ring, each of said rings being attached, either directly or through a linker, to the pyrimidinyl moiety. A potassium ion channel modulator of the present invention ("modulator of the present invention") may be a compound (also referred to herein as a "compound of the present invention") or metal ion complex (also referred to herein as a "complex of the present invention"), as described below.

In one aspect, the potassium ion channel modulator is a compound according to Formula (I):

In Formula (I), A and B are independently substituted or unsubstituted 5- or 6-membered heterocycloalkyl, or substituted or unsubstituted 5- or 6-membered heteroaryl. The symbol

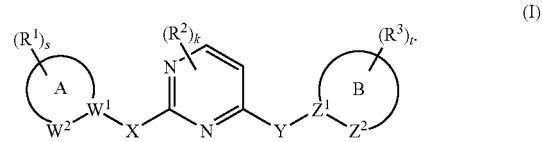

The symbol

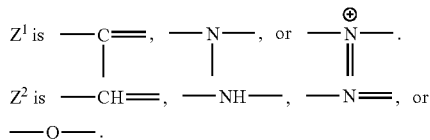

The symbol X is a bond, —CH$_2$—, or —NR$^4$—. Y is a bond, —CH=N—NH—, —NH—CH$_2$—, or —NR$^5$—. In some embodiments, X is a bond.

The symbols s and t are independently integers from 1 to 4. One of skill in the art will immediately recognize that where A is a 5-membered heterocycloalkyl or 5-membered heteroaryl, then s is an integer from 1 to 3; and where A is a 6-membered heterocycloalkyl or 6-membered heteroaryl, then s is an integer from 1 to 4. Likewise, where B is a 5-membered heterocycloalkyl or 5-membered heteroaryl, then t is an integer from 1 to 3 and where B is a 6-membered heterocycloalkyl or 6-membered heteroaryl, then t is an integer from 1 to 4.

The symbol k is an integer from 1 to 2.

R$^1$, R$^2$, and R$^3$ are independently H, —OH, —NH$_2$, —NO$_2$, —SO$_2$NH$_2$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, substituted or unsubstituted heteroaryl, or —NR$^7$R$^8$.

R$^7$ and R$^8$ are independently H, halogen, substituted or unsubstituted alkyl, substituted or unsubstituted heteroalkyl, substituted or unsubstituted 5- to 7-membered cycloalkyl, substituted or unsubstituted 5- to 7-membered heterocycloalkyl, substituted or unsubstituted aryl, or substituted or unsubstituted heteroaryl. R$^7$ and R$^8$ are optionally joined together with the nitrogen to which they are attached to form a substituted or unsubstituted 5- to 7-membered heterocycloalkyl, or substituted or unsubstituted heteroaryl.

R$^4$ and R$^5$ are independently H, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, or substituted or unsubstituted heteroaryl.

Where a plurality of R$^1$, R$^2$, and/or R$^3$ groups are present, each R$^1$, R$^2$, and/or R$^3$ group is optionally different. For example, where s is greater than one, then each R$^1$ is optionally different; where k is greater than one, then each R$^2$ is optionally different; and where t is greater than one, then each R$^3$ is optionally different.

R$^1$, R$^2$, and R$^3$ may optionally form part of a fused ring system. For example, two R$^1$ groups are optionally joined together with the atoms to which they are attached to form a substituted or unsubstituted 5- to 7-membered ring; two R$^2$ groups are optionally joined together with the atoms to which they are attached to form a substituted or unsubstituted 5- to 7-membered ring; and two R$^3$ groups are optionally joined together with the atoms to which they are attached to form a substituted or unsubstituted 5- to 7-membered ring.

In some embodiments, A is substituted or unsubstituted heteroaryl. A may also be substituted or unsubstituted pyridinyl.

In other embodiments, A is

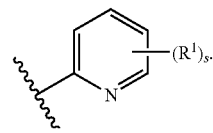

In Formula (III), R$^1$ and s are as defined above in the description of Formula (I). In some embodiments, R$^1$ is selected from H, halogen, —NH$_2$, substituted or unsubstituted alkyl, substituted or unsubstituted heteroalkyl, substituted or unsubstituted 5- to 7-membered cycloalkyl, substituted or unsubstituted 5- to 7-membered heterocycloalkyl, substituted or unsubstituted aryl, or substituted or unsubstituted heteroaryl.

A may also be

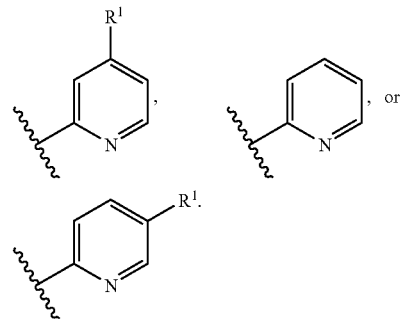

R$^1$ is as described above in the discussion of Formula (I) of Formula (III). Alternatively, R$^1$ is halogen, or substituted or unsubstituted alkyl. In a related embodiment, R$^1$ is Cl or unsubstituted alkyl (e.g. methyl, ethyl and the like). Thus, A may

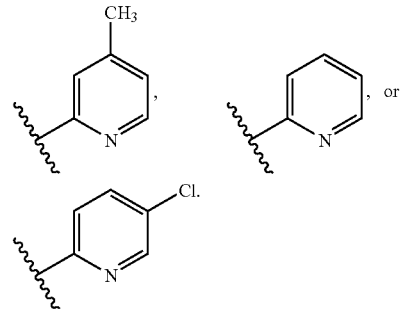

In other embodiments, B is substituted or unsubstituted heteroaryl. B may also be substituted or unsubstituted pyridinyl. Alternatively, B is

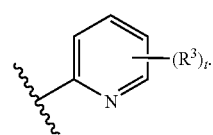

In Formula (II), $R^3$ and t are as defined above in the description of Formula (I). In some embodiments of Formula (II), $R^3$ is H, —$NH_2$, —$NO_2$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, or substituted or unsubstituted heteroaryl. In another embodiment, $R^3$ is Cl or —$NR^7R^8$. In a related embodiment, $R^3$ is —$NH_2$, —$N(CH_3)_2$,

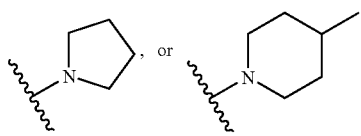

In other embodiments, B is

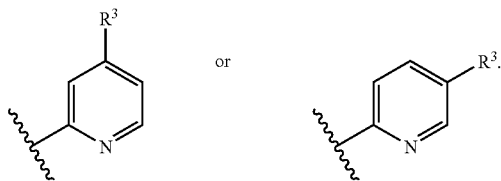

$R^3$ is as defined above in the description of Formula (I) or Formula (II). In other embodiments, $R^3$ is substituted or unsubstituted alkyl (e.g. methyl, ethyl, and the like). Thus, B may be

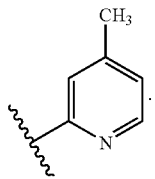

$R^1$, $R^2$, and $R^3$ may independently be H, —$NH_2$, —$NO_2$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, substituted or unsubstituted heteroaryl, or —$NR^7R^8$.

Alternatively, $R^1$ may be H, substituted or unsubstituted ($C_1$-$C_{10}$) alkyl, substituted or unsubstituted 2- to 10-membered heteroalkyl, or substituted or unsubstituted aryl. $R^1$ may also be H, methyl, —$NH_2$, or unsubstituted phenyl.

$R^2$ may be H, halogen, substituted or unsubstituted alkyl, substituted or unsubstituted heteroalkyl, substituted or unsubstituted 5- to 7-membered heterocycloalkyl, or substituted or unsubstituted aryl. $R^2$ may also be H, Cl, methyl, —$OCH_3$, or unsubstituted pyridinyl. In some embodiments, $R^2$ is H or —$OCH_3$.

$R^3$ may be H, —$NH_2$, —$NO_2$, halogen, substituted or unsubstituted ($C_1$-$C_1$) alkyl, substituted or unsubstituted 2- to 10-membered heteroalkyl, substituted or unsubstituted aryl, or substituted or unsubstituted heteroaryl. $R^3$ may also be H, —$NH_2$, —$NO_2$, Cl, Br, F, methyl, phenyl, fluorophenyl, —$CF_3$, —$OCH_3$, dimethylamino, unsubstituted piperidine, p-methyl morpholino, unsubstituted pyrrolidinonyl, unsubstituted 2-thiophenyl, unsubstituted 3-thiophenyl, unsubstituted furanyl, or n-methyl piperizinyl.

Alternatively, $R^3$ is Cl or —$NR^7R^8$, where $R^7$ and $R^8$ are as defined above.

$R^3$ may also be selected from $R^3$ is Cl, —$NH_2$, —$N(CH_3)_2$,

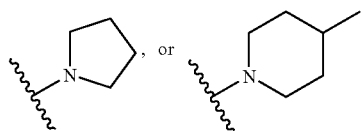

In some embodiments, X is a bond. In a related embodiment k is 2. In a further related embodiment, $R^2$ is H or —$OCH_3$.

In other embodiments, Y is NH. In a related embodiment, t is 1. In a further related embodiment, B is

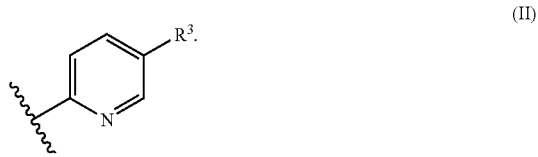

$R^3$ is as defined above in the description of Formula (II). In another related embodiment, B is

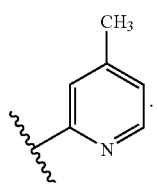

The symbol Y may also represent a bond. In a related embodiment, k is 1. In another related embodiment, $R^2$ is H.

X may be NH. In some related embodiments, A is

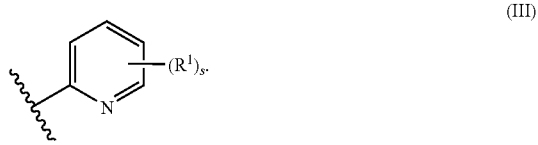

$R^1$ and s are as defined above in the description of Formula (III). In another related embodiment, A is

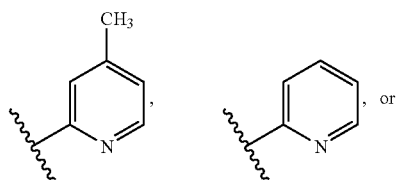

-continued

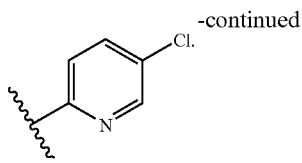

In some embodiments, each substituted moiety described above for the compounds of the present invention is substituted with at least one substituent group. The term "substituent group," as used herein, is defined in detail above in the "Abbreviations and Definitions" section. More specifically, in some embodiments, each substituted alkyl, substituted heteroalkyl, substituted cycloalkyl, substituted heterocycloalkyl, substituted aryl, and/or substituted heteroaryl described above are substituted with at least one substituent group. Each substituent group is optionally different. In other embodiments, at least one or all of these groups are substituted with at least one size-limited substituent group. Alternatively, at least one or all of these groups are substituted with at least one lower substituent group. Size-limited substituent groups and lower substituent groups are both defined in detail above in the "Abbreviations and Definitions" section.

In other embodiments, each substituted or unsubstituted alkyl is a substituted or unsubstituted $C_1$-$C_{20}$ alkyl, and each substituted or unsubstituted heteroalkyl is a substituted or unsubstituted 2- to 20-membered heteroalkyl.

Alternatively, each substituted or unsubstituted alkyl is a substituted or unsubstituted $C_1$-$C_8$ alkyl, and each substituted or unsubstituted heteroalkyl is a substituted or unsubstituted 2- to 8-membered heteroalkyl.

In another embodiment, the present invention provides a metal complex modulator, comprising a polyvalent metal ion (e.g. iron, zinc, copper, cobalt, manganese, and nickel) and a polydentate component of a metal ion chelator. The polydentate component is a compound of the present invention (e.g. a compound of Formulae (I), (II), or (III)). The metal complexes of the present invention are potassium ion channel modulators.

In some embodiments, the metal complex modulator has the structure

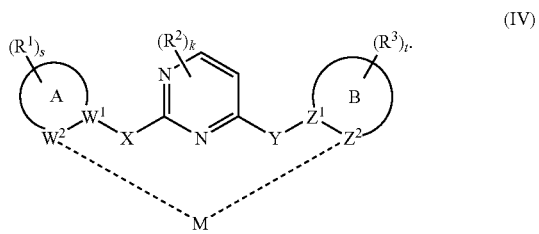

(IV)

In Formula (IV), M is a polyvalent metal ion (e.g. iron, zinc, copper, cobalt, manganese, and nickel). $W^2$ and $Z^2$ are —N═. $W^1$, $Z^1$, $R^1$, $R^2$, $R^3$, X, Y, s, k, t, A, and B are as defined above in the description of the compound of Formula (I).

Also within the scope of the present invention are compounds of the invention that function as poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or reactive analogues thereof are attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Preparation of Potassium Ion Channel Modulators

The following exemplary schemes illustrate methods of preparing the modulators of the present invention. These methods are not limited to producing the compounds shown, but can be used to prepare a variety of modulators such as the compounds and complexes described above. The modulators of the invention can also be produced by methods not explicitly illustrated in the schemes but are well within the skill of one in the art. The modulators can be prepared using readily available starting materials or known intermediates.

In the following schemes, the symbol Y is independently selected from $CH_2$, N, S, and O. The symbol D is independently selected from H, —OH, —$NH_2$, —$NO_2$, —$SO_2NH_2$, halogen, cyano, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, and substituted or unsubstituted heteroaryl. The symbol p is an integer independently selected from 1-5. The symbol q is an integer independently selected from 0-5.

The substituents of the pyrimidinyl compounds of the invention can be produced through the methods outlined in Schemes 1-8.

In one embodiment, the substituents of the invention comprise amino-substituted heteroaryl moieties as shown in Schemes 1-6.

Scheme 1

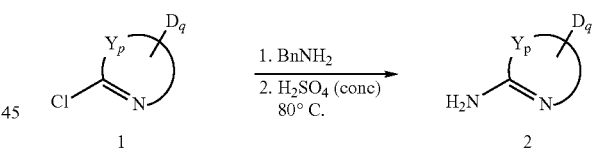

In Scheme 1, compound 1 is reacted with benzylamine, followed by debenzylation in concentrated sulfuric acid to produce 2.

An alternative route to producing compound 2 is shown in Scheme 2.

Scheme 2

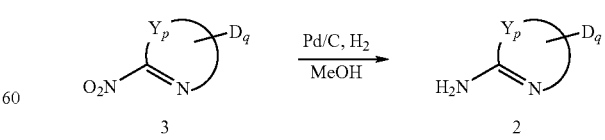

In Scheme 2, a compound 3 is reduced to form compound 2.

Substituents can be added to the amino-substituted heteroaryl moieties as described in Schemes 3-6.

Scheme 3

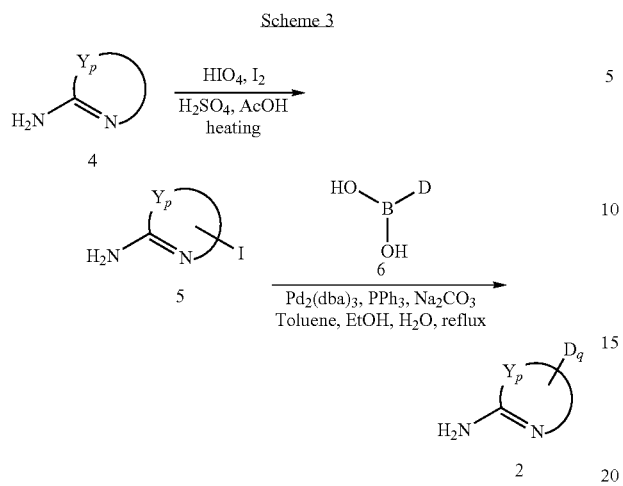

In Scheme 3, compound 4 is iodinated to produce a halo-substituted 2-amino-aza-heterocycle 5. This compound is reacted with a boronic acid 6 in the presence of tris(dibenzylideneacetone)dipalladium(0) (Pd$_2$(dba)$_3$), and PPh$_3$ in toluene, ethanol, and water to produce 2.

In another example, amino substituents can be added to the heteroaryl moieties in the following manner.

Scheme 4

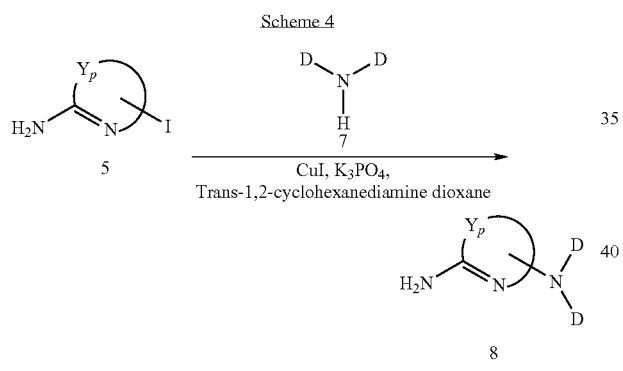

In Scheme 4, an iodo-substituted 2-amino-aza-heterocycle 5 is reacted with an amine 7 or amide using copper catalyzed coupling chemistry to generate a 2-amino-aza-heterocycle 8.

Scheme 5

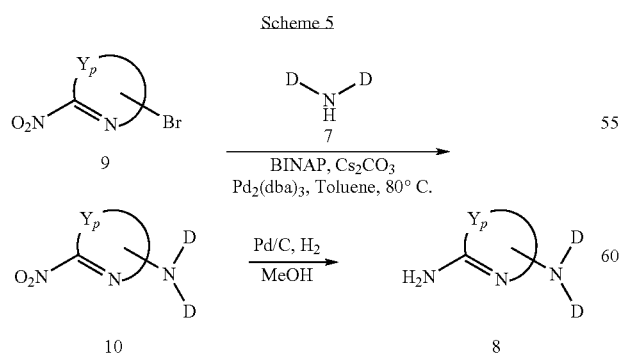

In Scheme 5, a bromo-substituted 2-nitro-aza-heterocycle 9 is reacted with an amine 7 or amide using palladium-catalyzed coupling chemistry to generate an aminosubstituted 2-nitro-aza-heterocycle 10. The nitro adduct is reduced to an amino adduct 8 by a palladium catalyzed hydrogenation.

Scheme 6

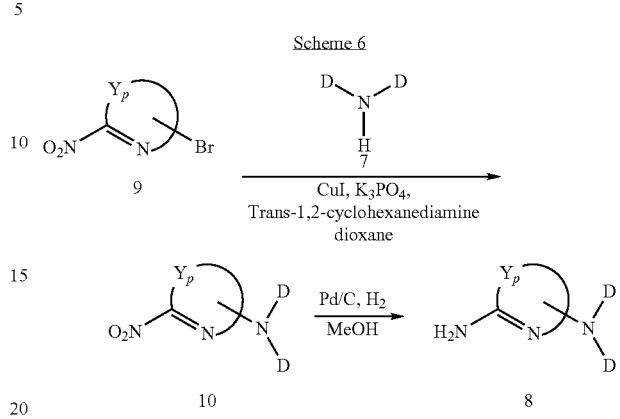

In Scheme 6, a bromo-substituted 2-nitro-aza-heterocycle 9 is reacted with an amine 7 or amide using copper catalyzed coupling chemistry to generate an aminosubstituted 2-nitro-aza-heterocycle 10. The nitro adduct is reduced to an amino adduct 8 by a palladium catalyzed hydrogenation.

In one embodiment, the substituents of the invention comprise halo-substituted heteroaryl moieties as shown in Scheme 7.

Scheme 7

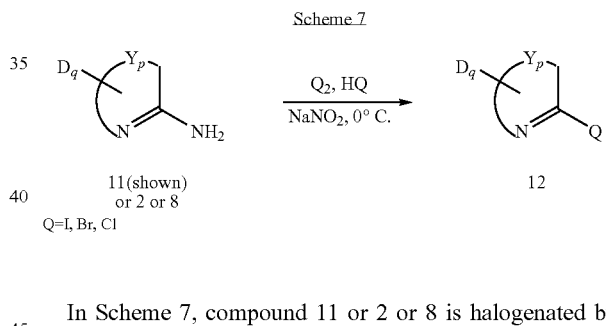

11(shown) or 2 or 8
Q=I, Br, Cl

In Scheme 7, compound 11 or 2 or 8 is halogenated by diazotization followed by sodium nitrite in the presence of acid containing halogen at 0° C. to produce compound 12.

In another embodiment, the substituents of the invention comprise stannyl-substituted heteroaryl moieties as shown in Scheme 8.

Scheme 8

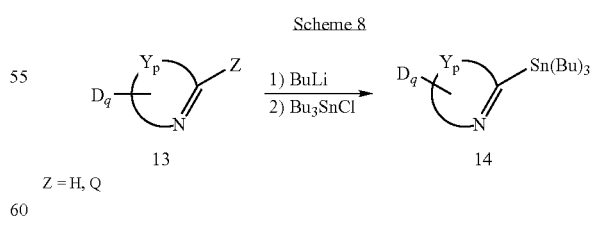

Z = H, Q

In Scheme 8, compound 13 is stannylated with n-butyl-lithium to produce compound 14.

Stannyl-substituted and halo-substituted heteroaryl moieties can be added to a pyrimidine compound of the invention through the methods outlined in Scheme 9.

Scheme 9

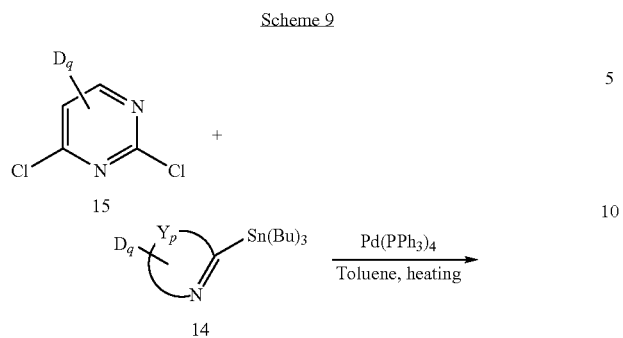

In Scheme 9, addition of compound 14 to a 2,4-dichloropyrimidine 15 in the presence of a palladium catalyst in toluene produces compound 16.

An alternative way of producing compound 16 is illustrated in Scheme 10.

Scheme 10

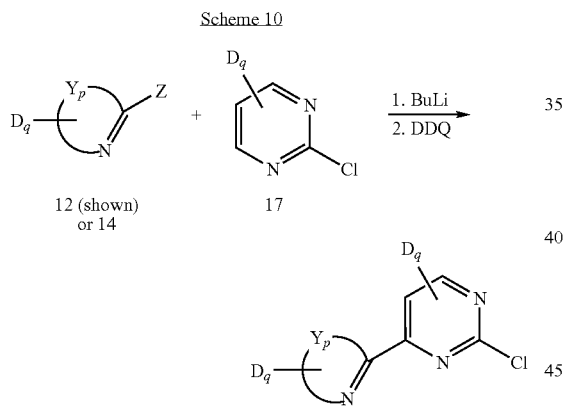

In Scheme 10, compound 12 or 14 is reacted with 2-chloropyrimidine 17 in the presence of n-butyllithium to produce 16.

Amino-substituted heteroaryl moieties can be added to a pyrimidine compound of the invention through the methods outlined in Scheme 11.

Scheme 11

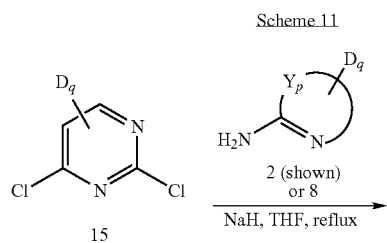

In Scheme 11, compound 2 or 8 is mixed with sodium hydride to facilitate the nucleophilic addition of 2 or 8 to compound 15 to form compound 18.

Bis-substituted pyrimidines are produced from the method of Scheme 12.

Scheme 12

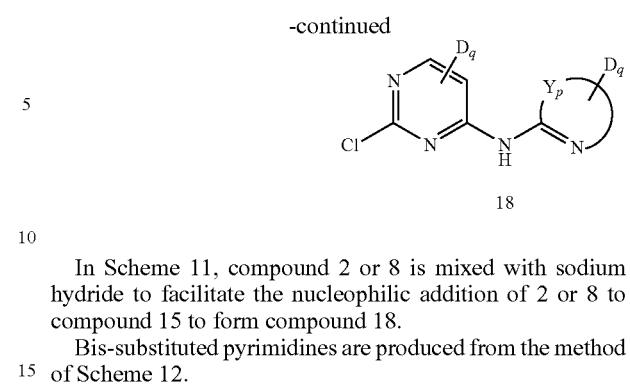

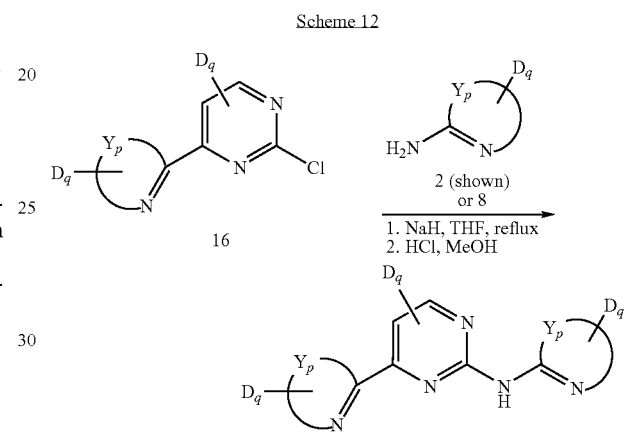

In Scheme 12, compound 2 or 8 is mixed with sodium hydride to facilitate the nucleophilic addition of 2 or 8 to compound 16. The final product is a bis-substituted pyrimidine 19.

An alternative method of producing bis-substituted pyrimidine compounds of the invention is illustrated by Scheme 13.

Scheme 13

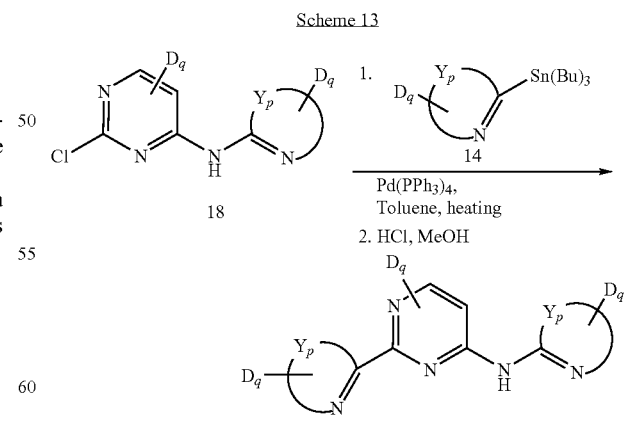

In Scheme 13, compound 14 is added to compound 18 in the presence of a palladium catalyst in toluene to produce the hydrochloride salt of a bis-substituted pyrimidine 20.

A method of making substituted pyrimidines with a fused aromatic ring is described in Scheme 14.

Scheme 14

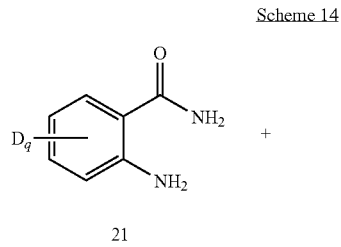

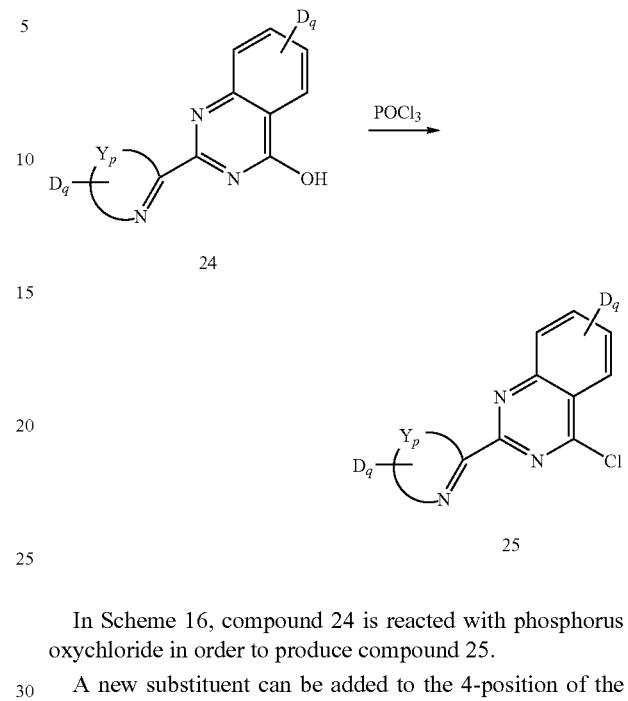

In Scheme 14, compound 21 is reacted with compound 22 in the presence of triethylamine in THF to provide compound 23.

The pyrimidine ring can be formed by a method outlined in Scheme 15.

Scheme 15

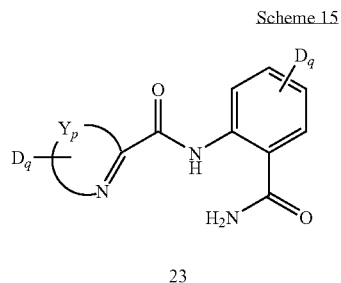

In Scheme 15, addition of a base causes the intramolecular cyclization of compound 23 to form compound 24.

The OH at the 4-position of the pyrimidine ring can be converted into a chlorine by the procedure outlined in Scheme 16.

In Scheme 16, compound 24 is reacted with phosphorus oxychloride in order to produce compound 25.

A new substituent can be added to the 4-position of the pyrimidine ring as shown in Scheme 17.

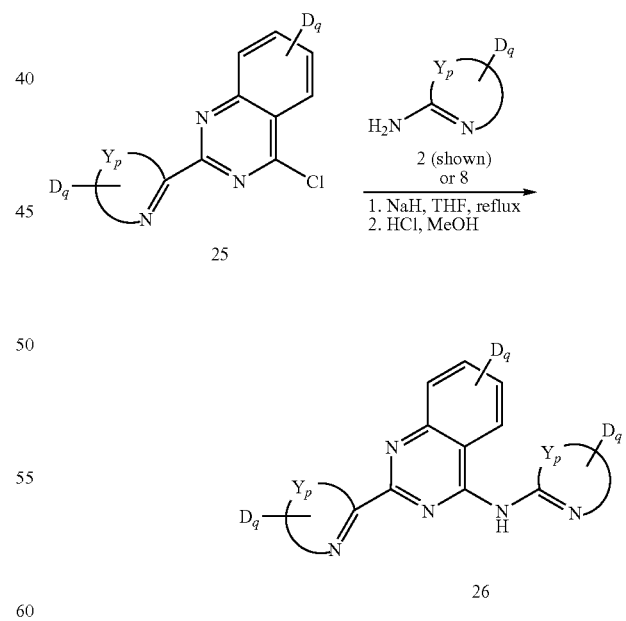

In Scheme 17, compound 2 or 8 is mixed with sodium hydride to facilitate the nucleophilic addition of 2 or 8 to compound 25. The product is a bis-substituted pyrimidine 26.

An alternative method of making substituted pyrimidines with a fused aromatic ring is described in Scheme 18.

Scheme 18

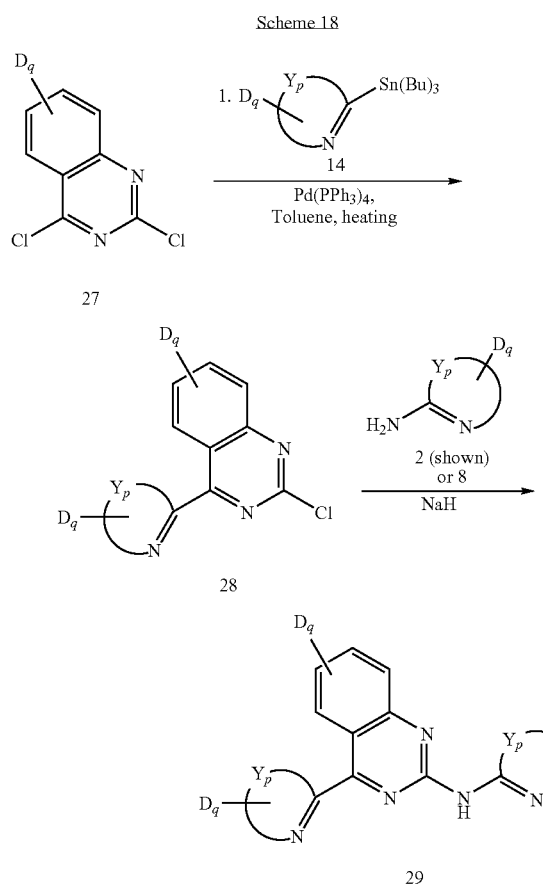

Compound 27 is reacted with stannyl derivative 14 in order to produce compound 28. Compound 28 is then reacted with compound 2 or 8. The product is a bis-substituted pyrimidine 29.

The compounds of the invention also include metal complexes. These metal complexes comprise a polyvalent metal ion and a pyrimidinyl compound of the invention. In an exemplary embodiment, the polyvalent metal ion can be a transition metal. In another exemplary embodiment, the polyvalent metal ion is a member selected from iron, zinc, copper, cobalt, manganese, and nickel.

A method of creating metal-pyrimidinyl complexes of the invention is outlined in Scheme 19.

Scheme 19

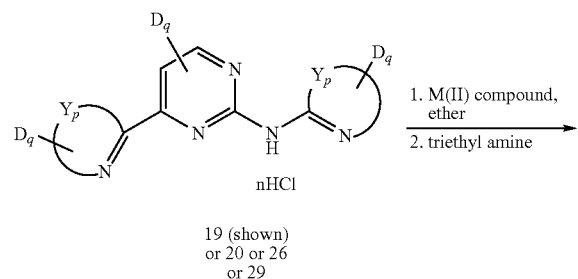

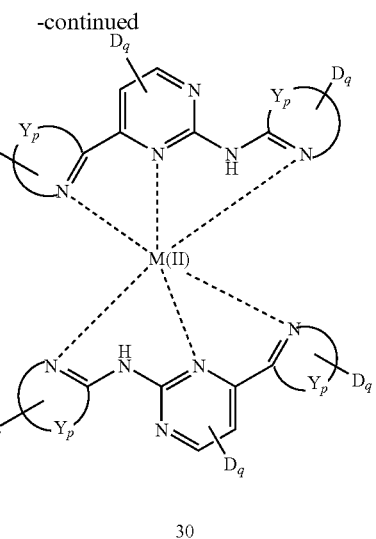

In Scheme 19, compound 19 or 20 or 26 or 29, or combinations thereof, are first mixed with FeClO$_4$ in ether. To this mixture is added triethylamine which then forms metal complex 30.

III. Assays for Modulators of Potassium Ion Channels

SK monomers as well as SK alleles and polymorphic variants are subunits of potassium ion channels. The activity of a potassium ion channel comprising SK subunits can be assessed using a variety of in vitro and in vivo assays, e.g., measuring current, measuring membrane potential, measuring ion flow, e.g., potassium or rubidium, measuring potassium concentration, measuring second messengers and transcription levels, using potassium-dependent yeast growth assays, and using e.g., voltage-sensitive dyes, radioactive tracers, and patchClamp electrophysiology.

Furthermore, such assays can be used to test for inhibitors and activators of channels comprising SK. The SK family of channels is implicated in a number of disorders that are targets for a therapeutic or prophylactic regimen, which functions by blockade or inhibition of one or more members of the SK channel family. The modulators and methods of the invention are useful to treat central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases). The modulators of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

Modulators of the potassium ion channels are tested using biologically active SK, either recombinant or naturally occurring, or by using native cells, like cells from the nervous system expressing an SK channel. SK channels can be isolated, co-expressed or expressed in a cell, or expressed in a membrane derived from a cell. In such assays, SK is expressed alone to form a homomeric potassium ion channel or is co-expressed with a second subunit (e.g., another SK family member) so as to form a heteromeric potassium ion channel. Modulation is tested using one of the in vitro or in vivo assays described above. Samples or assays that are treated with a potential potassium ion channel inhibitor or activator are compared to control samples without the test modulator, to examine the extent of modulation. Control samples (untreated with activators or inhibitors) are assigned a relative potassium ion channel activity value of 100. Inhibition of channels comprising SK is achieved when the potassium ion channel activity value relative to the control is less than 70%, preferably less than 40% and still more preferably, less than 30%. Modulators that decrease the flow of ions will cause a detectable decrease in the ion current density by decreasing the probability of a channel comprising SK being open, by decreasing conductance through the channel, and decreasing the number or expression of channels.

Changes in ion flow may be assessed by determining changes in polarization (i.e., electrical potential) of the cell or membrane expressing the potassium ion channel. A preferred means to determine changes in cellular polarization is by measuring changes in current or voltage with the voltageClamp and patchClamp techniques, using the "cell-attached" mode, the "inside-out" mode, the "outside-out" mode, the "perforated cell" mode, the "one or two electrode" mode, or the "whole cell" mode (see, e.g., Ackerman et al., *New Engl. J. Med.* 336: 1575-1595 (1997)). Whole cell currents are conveniently determined using the standard methodology (see, e.g., Hamil et al., *Pflugers. Archiv.* 391: 85 (1981)). Other known assays include: radiolabeled rubidium flux assays and fluorescence assays using voltage-sensitive dyes (see, e.g., Vestergarrd-Bogind et al., *J. Membrane Biol.* 88: 67-75 (1988); Daniel et al., *J. Pharmacol. Meth.* 25: 185-193 (1991); Holevinsky et al., *J. Membrane Biology* 137: 59-70 (1994)). Assays for modulators capable of inhibiting or increasing potassium flow through the channel proteins can be performed by application of the modulators to a bath solution in contact with and comprising cells having a channel of the present invention (see, e.g., Blatz et al., *Nature* 323: 718-720 (1986); Park, *J. Physiol.* 481: 555-570 (1994)). Generally, the modulators to be tested are present in the range from about 1 pM to about 100 mM, preferably from about 1 pM to about 1 µM.

The effects of the test modulators upon the function of the channels can be measured by changes in the electrical currents or ionic flow or by the consequences of changes in currents and flow. Changes in electrical current or ionic flow are measured by either increases or decreases in flow of ions such as potassium or rubidium ions. The cations can be measured in a variety of standard ways. They can be measured directly by concentration changes of the ions or indirectly by membrane potential or by radio-labeling of the ions. Consequences of the test modulator on ion flow can be quite varied. Accordingly, any suitable physiological change can be used to assess the influence of a test modulator on the channels of this invention. The effects of a test modulator can be measured by a toxin-binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as calcium, or cyclic nucleotides.

IV. Pharmaceutical Compositions for use as Potassium Ion Channel Modulators

In another aspect, the present invention provides pharmaceutical compositions comprising a pharmaceutically acceptable carrier and a modulator of the present invention (e.g. a compound of the present invention or a complex of the present invention).

Formulation of the Modulators

The modulators of the present invention can be prepared and administered in a wide variety of oral, parenteral and topical dosage forms. Thus, the modulators of the present invention can be administered by injection, that is, intravenously, intramuscularly, intracutaneously, subcutaneously, intraduodenally, or intraperitoneally. Also, the modulators described herein can be administered by inhalation, for example, intranasally. Additionally, the modulators of the present invention can be administered transdermally. Accordingly, the present invention also provides pharmaceutical compositions comprising a pharmaceutically acceptable carrier and either a modulator, or a pharmaceutically acceptable salt of a modulator.

For preparing pharmaceutical compositions from the modulators of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active modulator. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active modulator with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

V. Methods for Decreasing Ion Flow in Potassium Ion Channels

In yet another aspect, the present invention provides a method for decreasing ion flow through potassium ion channels in a cell, comprising contacting the cell with a potassium ion channel modulating amount of a modulator of the present invention.

In an exemplary embodiment, the potassium ion channels comprise at least one SK subunit.

The methods provided in this aspect of the invention are useful in the therapy of conditions mediated through potassium ion flow, as well as for the diagnosis of conditions that can be treated by decreasing ion flow through potassium ion channels. Additionally the methods are useful for determining if a patient will be responsive to therapeutic agents which act by modulating potassium ion channels. In particular, a patient's cell sample can be obtained and contacted with a potassium ion channel modulator described above and the ion flow can be measured relative to a cell's ion flow in the absence of the modulator. A decrease in ion flow will typically indicate that the patient will be responsive to a therapeutic regiment of the modulator.

VI. Methods for Treating Conditions Mediated by Potassium Ion Channels

In still another aspect, the present invention provides a method for treating a disease through the modulation of potassium ion flow through potassium ion channels. The modulation may be activation or inhibition of the potassium ion flow. Thus, the modulators of the present invention may be inhibitors of potassium ion flow through potassium ion channels (i.e. decrease the flow relative to the absence of the modulator) or activators of potassium ion flow through potassium ion channels (i.e. increase the flow relative to the absence of the modulator).

The modulators are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), and as neuroprotective agents (e.g., to prevent stroke and the like). The modulators of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression. This method involves administering, to a patient, an effective amount (e.g. a therapeutically effective amount) of a modulator of the present invention (a compound or complex of the present invention).

Thus, the present invention provides a method of decreasing ion flow through potassium ion channels in a cell. The method includes contacting the cell with a potassium ion channel-modulating amount of a modulator of the present invention. In some embodiments, the potassium ion channel includes at least one SK subunit. The cell may be isolated or form part of a organ or organism.

The modulators provided herein find therapeutic utility via modulation of potassium ion channels in the treatment of diseases or conditions. The potassium ion channels that are typically modulated are described herein. As noted above, these channels may include homomultimers and heteromultimers.

In therapeutic use for the treatment of neurological conditions, the modulators utilized in the pharmaceutical method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the modulator being employed. Determination of the proper dosage for a particular situation is within the skill of the practitioner. Generally, treatment is initiated with smaller dosages, which are less than the optimum dose of the modulator. Thereafter, the dosage is increased by small increments until the optimum effect under the circumstances is reached. For convenience, the total daily dosage may be divided and administered in portions during the day.

The materials and methods of the present invention are further illustrated by the examples which follow. These examples are offered to illustrate, but not to limit, the claimed invention.

EXAMPLES

General

In the examples below, unless otherwise stated, temperatures are given in degrees Celsius (° C.); operations were carried out at room or ambient temperature, "rt," or "RT," (typically a range of from about 18-25° C.); evaporation of solvent was carried out using a rotary evaporator under reduced pressure (typically, 4.5-30 mm Hg) with a bath temperature of up to 60° C.; the course of reactions was typically followed by thin layer chromatography (TLC) and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

Unless otherwise specified, all solvents (HPLC grade) and reagents were purchased from suppliers and used without further purification. Reactions were conducted under a blanket of argon unless otherwise stated. Analytical TLC was performed on Whatman Inc. 60 silica gel plates (0.25 mm thickness). Compounds were visualized under UV lamp (254 nM) or by developing with $KMnO_4$/KOH, ninhydrin or Hanessian's solution. Flash chromatography was done using silica gel from Selectro Scientific (particle size 32-63). $^1$HNMR, $^{19}$F NMR and $^{13}$C NMR spectra were recorded on a Varian 300 machine at 300 MHz, 282 MHz and 75.7 MHz, respectively. Melting points were recorded on a Electrothermal IA9100 apparatus and were uncorrected.

Example 1

Preparation of 2 from 1
 1.1 Nucleophilic Replacement

A mixture of 14.7 mmol of 1 and 75 mmol of benzylamine was heated at 220° C. for 6 h in a sealed tube. The reaction mixture was concentrated in vacuo and the residue was purified by column chromatography on silica gel to give 7.0 mmol of N-benzyl pyridine-2-amine.

A solution of 6.9 mmol of N-benzyl pyridin-2-amine in 15 mL of conc. $H_2SO_4$ was stirred at 80° C. for 1 h. The reaction mixture was poured into crushed ice and neutralized with 28% $NH_4OH$. The mixture was extracted with AcOEt and the organic phase was washed with brine, dried over $MgSO_4$, and concentrated in vacuo. The residue was purified by column chromatography on silica gel to give 5.0 mmol of 2.

1.2 Results

Analytical data for exemplary compounds of structure 2 are provided below.

1.2.a 5-Hexylpyridin-2-ylamine $^1$H NMR (300 MHz, $CDCl_3$) δ 7.88 (d, J=2.2 Hz, 1H), 7.26 (dd, $J_1$=8.4 Hz, $J_2$=2.2 Hz, 1H), 6.45 (d, J=8.4 Hz, 1H), 4.27 (br s, 2H), 2.45 (d, J=6.6 Hz, 1H), 1.48-1.56 (m, 2H),1.27-1.35 (m, 6H), 0.88 (t, J=6.6 Hz, 3H); MS m/z: 178 (M+1).

1.2.b 5-tert-Butylpyridin-2-ylamine $^1$H NMR (300 MHz, $CDCl_3$) δ 8.08 (d, J=2.6 Hz, 1H), 7.47 (dd, J,=8.6 Hz, $J_2$=2.6 Hz, 1H), 6.47 (dd, $J_1$=8.6 Hz, $J_2$=0.7 Hz, 1H), 1.28 (s, 9H); MS m/z: 151 (M+1).

1.2.c 5-[2-(Benzyloxy)ethyl]pyridin-2-ylamine $^1$H NMR (300 MHz, $CDCl_3$) δ 7.94 (d, J=1.8 Hz, 1H), 7.25-7.37 (m, 6H), 6.45 (dd, $J_1$=8.4 Hz, $J_2$=0.7 Hz, 1H), 4.51 (s, 2H), 4.31 (br s, 2H), 3.62 (t, J=6.9 Hz, 2H), 2.78 (t, J=6.9 Hz, 2H); MS m/z: 228 (M+1).

1.2.d
1-(6-Aminopyridin-3-yl)-4-methylpiperazin-2-one $^1$H NMR (300 MHz, DMSO-$d_6$) δ 7.80 (d, J=2.4 Hz, 1H), 7.28 (dd, $J_3$=8.7 Hz, $J_2$ =2.7 Hz, 1H), 6.43 (d, J=8.8 Hz, 1H), 5.97 (br s, 2H), 3.53 (t, J=5.4 Hz, 2H), 3.06 (s, 2H), 2.68 (t, J=5.4 Hz, 2H), 2.26 (s, 3H); MS m/z: 279 (M+1).

Example 2

Preparation of 2 from 3
 2.1 Catalytic Reduction

A solution or a suspension of 15 mmol of 3 and 0.5 g of Pd/C (10%) in 150 mL of methanol was stirred overnight under $H_2$ (1 atm). After filtering through celite, the solution was concentrated under a reduced pressure to give 15 mmol of 2.

Example 3

Preparation of 2
 3.1 Iodination of 4

A mixture of 240 mmol of 4, 58 mmol of $HIO_4$, and 240 mmol of $I_2$ in 60 mL of water, 4 mL of concentrated $H_2SO_4$, and 200 mL of acetic acid was stirred at 80° C. for 4 h. Excess $I_2$ was neutralized by the addition of 200 mL of saturated $Na_2S_2O_3$ solution. The resulting aqueous solution was extracted with EtOAc. The organic phase was washed with saturated NaCl, dried over $MgSO_4$, and concentrated under a reduced pressure. The residue was purified by column chromatography on silica gel to give 136 mmol of 5.

3.2 Suzuki Cross Coupling

A mixture of 15 mmol of 5, 15 mmol of 6, 0.35 mmol of $Pd_2(dba)_3$, and 2.4 mmol of $PPh_3$ in 40 mL of toluene, 20 mL of ethanol, and 20 mL of water was refluxed overnight under $N_2$. The reaction mixture was diluted with 300 mL of ethyl acetate and the organic solution was washed with saturated NaCl, dried over $MgSO_4$, and concentrated under a reduced pressure. The residue was purified by column chromatography on silica gel to give 13.1 mmol of 2.

3.3 Results

Analytical data for exemplary compounds of structure 2 are provided below.

3.3.a 5-(2-Methoxy-phenyl)-pyridin-2-ylamine $^1$H NMR (300 MHz, DMSO-$d_6$) δ 7.99 (d, J=2.0 Hz, 1H), 7.48 (dd, $J_1$=8.6 Hz, $J_2$=2.3 Hz, 1H), 7.26 (d, J=7.5 Hz, 1H), 7.21 (d, J=6.1 Hz, 1H), 7.03 (d, J=8.0 Hz, 1H), 6.96 (t, J=7.3 Hz, 1H), 6.44 (d, J=8.5 Hz, 1H), 5.94 (s, 2H), 3.73 (s, 3H); MS m/z: 201 (M+1).

3.3.b (5-Methyl-furan-2-yl)-pyridin-2-ylamine $^1$H NMR (300 MHz, DMSO-$d_6$) δ 8.17 (d, J=2.0 Hz, 1H), 7.63-7.52 (m, 2H), 6.48 (d, J=3.2 Hz, 1H), 6.43 (d, J=8.7 Hz, 1H), 6.08 (s, 2H), 2.27 (s, 3H); MS m/z: 175 (M+1).

3.3.c [3,3']Bipyridinyl-6-ylamine $^1$H NMR (300 MHz, DMSO-$d_6$) δ 8.78 (d, J=2.1 Hz, 1H), 8.44 (dd, $J_1$=4.9 Hz, $J_2$=1.6 Hz, 1H), 8.27 (d, J=2.2 Hz, 1H), 7.94 (dt, $J_1$=8.0 Hz, $J_2$=1.9 Hz, 1H), 7.73 (dd, $J_1$=8.7 Hz, $J_2$=2.6 Hz, 1H), 7.38 (dd, $J_1$=8.7 Hz, $J_2$=2.6 Hz, 1H), 6.52 (d, J=8.7 Hz, 1H), 6.17 (s, 2H); MS m/z: 172 (M+1).

3.3.d
5-(4-Fluoro-phenyl)-4-methyl-pyridin-2-ylamine $^1$H NMR (300 MHz, DMSO-$d_6$) δ 7.68 (s, 1H), 7.30 (dd, $J_1$=8.5 Hz, $J_2$=5.7 Hz, 2H), 7.19 (t, J=8.9 Hz, 2H), 6.33 (s, 1H), 5.87 (s, 2H), 2.07 (s, 3H); MS m/z: 203 (M+1).

3.3.e 5-(3-Fluoro-phenyl)-pyridin-2-ylamine $^1$H NMR (300 MHz, DMSO-d$_6$) δ 8.27 (d, J=2.3 Hz, 1H), 7.71 (d, J=8.6 Hz, 1H), 7.42-7.38 (m, 3H), 7.08-7.01 (m, 1H), 6.49 (d, J=8.6 Hz, 1H), 6.15 (s, 2H); MS m/z: 189 (M+1).

3.3.f 5-Thiophen-2-yl-pyridin-2-ylamine $^1$H NMR (300 MHz, DMSO-d$_6$) δ 8.19 (d, J=2.3 Hz, 1H), 7.61 (d, J=8.5 Hz, 1H), 7.37 (d, J=5.1 Hz, 1H), 7.25 (d, J=3.3 Hz, 1H), 7.04 (t, J=4.7 Hz, 1H), 6.45 (d, J=8.7 Hz, 1H), 6.14 (s, 2H); MS m/z: 177 (M+1).

Example 4

Preparation of 8 from 5
4.1 Ullmann Cross-Coupling

To a solution of 50.0 mmol of 5 and 60.0 mmol of 7 in 50.0 mL of 1,4-dioxane was added 0.500 mmol of copper (I) iodide followed by the addition of 100 mmol of K$_3$PO$_4$ and 5 mmol of trans-cyclohexanediamine, then the resulting mixture was stirred at 100° C. for 16 h. The reaction mixture was cooled to rt and diluted with 500 mL of H$_2$O. The resulting aqueous solution was extracted with CHCl$_3$. The organic phase was washed with saturated NaCl, dried over MgSO$_4$ and concentrated in vacuo. The crude product was purified by column chromatography to give 43.4 mmol of 8.

4.2 Results

Analytical data for exemplary compounds of structure 8 are provided below.

4.2.a tert-Butyl 4-(6-aminopyridin-3-yl)-3-oxopiperazine-1-carboxylate $^1$H NMR (400 MHz, CDCl$_3$) δ 7.97-8.00 (m, 1H), 7.35-7.40 (m, 1H), 6.50-6.54 (m, 1H), 4.54 (br s, 2H), 4.24 (s, 2H), 3.65-3.69 (m, 2H), 3.75-3.80 (m, 2H), 1.50 (s, 9H); MS m/z: 293 (M+1).

4.2.b 5-(4-Methyl-1,4-diazepan-1-yl)pyridin-2-ylamine $^1$H NMR (400 MHz, DMSO-d$_6$) δ 7.46 (d, J=3.5 Hz, 1H), 6.95 (dd, J$_3$=8.8 Hz, J$_2$=3.5 Hz, 1H), 6.38 (d, J=8.8 Hz, 1H), 5.04 (br s, 2H), 3.26-3.40 (m, 4H), 2.53-2.59 (m, 2H), 2.41-2.47 (m, 2H), 2.24 (s, 3H), 1.78-1.90 (m, 2H); MS m/z: 207 (M+1).

4.2.c 4-(6-Aminopyyridin-3-yl)-1-methyl-1,4-diazepan-5-one $^1$H NMR (400 MHz, DMSO-d$_6$) δ 7.71 (d, J=2.9 Hz, 1H), 7.18 (dd, J$_3$=8.8 Hz, J$_2$=2.9 Hz, 1H), 6.41 (d, J=8.8 Hz, 1H), 5.90 (br s, 2H), 3.64-3.71 (m, 2H), 2.51-2.62 (m, 4H), 2.26 (s, 3H); MS m/z: 221(M+1).

4.2.d tert-Butyl 4-(6-aminopyridin-3-yl)-5-oxo-1,4-diazepane-1-carboxylate $^1$H NMR (400 MHz, CDCl$_3$) δ 7.90 (d, J=2.8 Hz, 1H), 7.29 (dd, J$_1$=8.8 Hz, J$_2$=2.8 Hz, 1H), 6.50 (d, J=8.8 Hz, 1H), 4.54 (br s, 2H), 3.71-3.75 (m, 6H), 2.80-2.83 (m, 2H), 1.49 (s, 9H); MS m/z: 307 (M+1).

Example 5

Preparation of 8
5.1 Buchwald Cross-Coupling

A mixture of 30 mmol of 9, 30 mmol of 7, 0.04 mmol of Pd$_2$(dba)$_3$, 0.08 mmol of rac-2,2'-bis(phenylphosphino)-1,1'-binaphthyl (BINAP), and 42 mmol of Cs$_2$CO$_3$ in 100 mL of dry toluene was stirred at 80° C. for two days under N$_2$. The reaction mixture was diluted with 400 mL of ethyl acetate and the organic solution was washed with saturated NaCl, dried over MgSO$_4$, and concentrated under reduced pressure. The residue was crystallized in ethyl acetate to yield 15.8 mmol of 10.

A solution or a suspension of 15 mmol of 10 and 0.5 g of Pd/C (10%) in 150 mL of methanol was stirred overnight under H$_2$ (1 atm). After filtering through celite, the solution was concentrated under a reduced pressure to give 15 mmol of 8.

5.2 Results

Analytical data for exemplary compounds of structure 8 are provided below.

5.2.a 5-(4-Methyl-piperazin-1-yl)-pyridin-2-ylamine $^1$H NMR (300 MHz, DMSO-d$_6$) δ 7.56 (d, J=2.7 Hz, 1H), 7.13 (dd, J$_1$=8.9 Hz, J$_2$=2.9 Hz, 1H), 6.36 (d, J=8.8 Hz, 1H), 5.36 (s, 2H), 2.89 (t, J=5.0 Hz, 4H), 2.40 (t, J=5.0 Hz, 4H), 2.18 (s, 3H); MS m/z: 193 (M+1).

5.2.b 4-Methyl-3,4,5,6-tetrahydro-2H-[1,3']bipyridinyl-6'-ylamine $^1$H NMR (300 MHz, DMSO-d$_6$) δ 7.56 (d, J=2.8 Hz, 1H), 7.11 (dd, J$_1$=8.9 Hz, J$_2$=3.0 Hz, 1H), 6.35 (d, J=8.8 Hz, 1H), 5.34 (s, 2H), 3.26 (d, J=12.0 Hz, 2H), 2.45 (dt, J$_1$=9.3 Hz, J$_2$=4.2 Hz, 2H), 1.64 (d, J=12.5 Hz, 2H), 1.4-1.3 (m, 1H), 1.44-1.28 (m, 2H), 0.90 (d, J=6.5 Hz, 3H); MS m/z: 192 (M+1).

5.2.c 1-(6-Aminopyridin-3-yl)-pyrrolidin-2-one $^1$H NMR (300 MHz, DMSO-d$_6$) δ 8.03 (d, J=2.6 Hz, 1H), 7.63 (dd, J$_1$=8.9 Hz, J$_2$=2.6 Hz, 1H), 6.42 (d, J=8.9 Hz, 1H), 5.83 (s, 2H), 3.70 (t, J=7.0 Hz, 2H), 2.39 (t, J$_1$=7.8 Hz, 2H), 2.01 (dd, J$_1$=7.1 Hz, J$_2$=7.9 Hz, 2H); MS m/z: 178 (M+1).

5.2.d 1-(6-Aminopyridin-3-yl)piperidin-2-one $^1$H NMR (400 MHz, DMSO-d$_6$) δ 7.76 (d, J=2.4 Hz, 1H), 7.24 (dd, J$_3$=8.8 Hz, J$_2$=2.4 Hz, 1H), 6.42 (d, J=8.8 Hz, 1H), 5.90 (br s, 2H), 3.49 (t, J=6.0 Hz, 2H), 2.34 (t, J=6.0 Hz, 2H), 1.77-1.85 (m, 4H); MS m/z: 192 (M+1).

5.2.e 1-(6-Aminopyridin-3-yl)piperidin-4-ol $^1$H NMR (400 MHz, DMSO-d$_6$) δ 7.59 (d, J=2.4 Hz, 1H), 7.14 (dd, J$_1$=9.2 Hz, J$_2$=2.4 Hz, 2H), 6.38 (d, J=9.2 Hz, 1H), 5.34 (br s, 2H), 4.63 (1H, d, J=4.4 Hz), 3.50-3.57 (m, 1H), 3.18-3.23 (m, 2H), 2.59-2.65 (m, 2H), 1.76-1.83 (m, 2H), 1.44-1.54 (m, 2H); MS m/z: 194 (M+1).

5.2.f 5-Piperidin-1-ylpyridin-2-ylamine $^1$H NMR (400 MHz, CDCl$_3$) δ 7.79 (d, J=2.8 Hz, 1H), 7.17 (dd, J$_1$=8.8 Hz, J$_2$=2.8 Hz, 1H), 6.47 (dd, J$_3$=8.0 Hz, J$_2$=0.8

Hz, 1H), 4.11 (br s, 2H), 2.98 (d, J=5.2 Hz, 2H), 2.97 (d, J=5.2 Hz, 2H), 1.68-1.74 (m, 4H), 1.51-1.57 (m, 2H); MS m/z: 178 (M+1).

5.2.g 5-(4-Isopropylpiperazin-1-yl)pyridin-2-ylamine $^1$H NMR (300 MHz, DMSO-$d_6$) δ 7.55-7.60 (m, 1H), 7.10-7.17 (m, 1H), 6.35-6.42 (m, 1H), 5.34 (br s, 2H), 2.85-2.94 (m, 4H), 2.50-2.70 (m, 5H), 0.95-1.02 (m, 6H); MS m/z: 221 (M+1).

5.2.h tert-Butyl 4-(6-aminopyridin-3-yl)piperazine-1-carboxylate $^1$H NMR (400 MHz, CDCl$_3$) δ 7.78 (d, J=2.8 Hz, 1H), 7.17 (dd, J$_1$=8.8 Hz, J$_2$=2.8 Hz, 1H), 6.49 (d, J=8.8 Hz, 1H), 4.21 (br s, 2H), 3.57 (t, J=5.2 Hz, 4H), 2.96 (t, J=5.2 Hz, 4H), 1.48 (s, 9H); MS m/z: 279 (M+1).

5.2.i 1-(6-Aminopyridin-3-yl)-4-methylpiperazin-2-one $^1$H NMR (300 MHz, DMSO-$d_6$) δ 7.80 (d, J=2.4 Hz, 1H), 7.28 (dd, J$_3$=8.7 Hz, J$_2$=2.7 Hz, 1H), 6.43 (d, J=8.8 Hz, 1H), 5.97 (br s, 2H), 3.53 (t, J=5.4 Hz, 2H), 3.06 (s, 2H), 2.68 (t, J=5.4 Hz, 2H), 2.26 (s, 3H); MS m/z: 207 (M+1).

5.2.j 5-[3-(Dimethylamino)pyrrolidin-1-yl]pyridin-2-ylamine $^1$H NMR (400 MHz, CDCl$_3$) δ 7.78 (d, J=2.8 Hz, 1H), 6.83 (dd, J$_1$=8.8 Hz, J$_2$=2.8 Hz, 1H), 6.49 (d, J=8.8 Hz, 1H), 3.96 (br s, 2H), 3.24-3.41 (m, 3H), 3.09 (t, J=8.0 Hz, 1H), 2.82-2.90 (m, 1H), 2.35 (s, 6H), 2.14-2.22 (m, 1H), 1.86-1.96 (m, 1H); MS m/z: 206 (M+1).

5.2.k N$^5$-1-Azabicyclo[2.2.2]oct-3-ylpyridin-2,5-yldiamine $^1$H NMR (400 MHz, CDCl$_3$) δ 7.56 (d, J=2.8 Hz, 1H), 6.86 (dd, J$_1$=8.4 Hz, J$_2$=2.8 Hz, 1H), 6.44 (d, J=8.4 Hz, 1H), 4.00 (br s, 2H), 3.34-3.37 (m, 1H), 2.80-2.90 (m, 4H), 2.50-2.53 (m, 1H), 1.23-1.97 (m, 6H); MS m/z: 218 (M+1).

5.2.l 5-(2,4,5-Trimethylpiperazin-1-yl)pyridin-2-ylamine $^1$H NMR (400 MHz, CDCl$_3$) δ 7.91 (d, J=2.8 Hz, 1H), 7.30 (dd, J$_1$=8.8 Hz, J$_2$=2.8 Hz, 1H), 6.49 (d, J=8.8 Hz, 1H), 4.29 (br s, 2H), 3.06 (m, 1H), 2.86 (dd, J$_1$ 11.2 Hz, J$_2$=3.2 Hz, 2H), 2.66 (m, 1H), 2.33 (m, 4H), 2.12 (t, J=10.8 Hz, 1H), 1.07 (d, J=6.4 Hz, 3H), 0.85 (d, J=6.4 Hz, 3H); MS m/z: 221 (M+1).

5.2.m N$^5$-Methyl-N$^5$-(1-methylpyrrolidin-3-yl)pyridin-2,5-yldiamine $^1$H NMR (400 MHz, CDCl$_3$) δ 7.78 (d, J=2.8 Hz, 1H), 7.16 (dd, J$_1$=8.8 Hz, J$_2$=2.8 Hz, 1H), 6.47 (d, J=8.8 Hz, 1H), 4.12 (br s, 2H), 3.97-4.04 (m, 1H), 2.72 (s, 3H), 2.60-2.70 (m, 2H), 2.50-2.56 (m, 2H), 2.34 (s, 3H), 2.04-2.10 (m, 1H), 1.77-1.83 (m, 1H); MS m/z: 207 (M+1).

5.2.n 5-(3-Methylpiperazin-1-yl)pyridin-2-ylamine $^1$H NMR (400 MHz, CDCl$_3$) δ 7.74 (d, J=2.8 Hz, 1H), 7.15 (dd, J$_1$=8.8 Hz, J$_2$=2.8 Hz, 1H), 6.48 (d, J=8.8 Hz, 1H), 4.33 (m, 1H), 4.21 (br s, 2H), 3.92-3.96 (m, 1H), 3.19-3.26 (m, 2H), 3.08-3.11 (m, 1H), 2.82 (dd, J$_1$=11.6 Hz, J$_2$=4.0 Hz, 1H), 2.61-2.68 (m, 1H), 1.48 (s, 9H), 1.32 (d, J=6.8 Hz, 3H); MS m/z: 293 (M+1).

5.2.o 5-(3,5-Dimethylpiperazin-1-yl)pyridin-2-ylamine $^1$H NMR (400 MHz, CDCl$_3$) δ 7.76 (d, J=2.8 Hz, 1H), 7.16 (dd, J$_1$=8.8 Hz, J$_2$=2.8 Hz, 1H), 6.50 (d, J=8.8 Hz, 1H), 4.18-4.24 (m, 2H), 3.08-3.11 (m, 2H), 2.80 (dd, J$_1$=11.6 Hz, J$_2$=4.0 Hz, 1H), 1.49 (s, 9H), 1.37 (d, J=6.8 Hz, 6H); MS m/z: 307 (M+1).

5.2.p N$^5$-(2-Methoxyethyl)-N$^5$-methylpyridin-2,5-yldiamine

MS m/z: 182 (M+1).

5.2.q 5-(4-Methoxypiperidin-1-yl)pyridin-2-ylamine

MS m/z: 208 (M+1).

Example 6

Preparation of 8

6.1 Ullmann Cross-Coupling

To a solution of 24.6 mmol of 9 and 27.3 mmol of 7 in 50 mL of 1,4-dioxane was added 4.92 mmol of copper (I) iodide followed by the addition of 49.2 mmol of K$_3$PO$_4$ and 4.92 mmol of trans-cyclohexanediamine, then the resulting mixture was stirred at 100° C. for 12 h. The reaction mixture was cooled to room temperature and concentrated in vacuo. The residue was diluted with CHCl$_3$, poured into water, and insoluble material was removed by celite filtration. The filtrate was extracted with CHCl$_3$, dried over MgSO$_4$ and concentrated in vacuo. The crude product was purified by column chromatography to give 7.87 mmol of nitro derivative.

A solution of 7.66 mmol of nitro derivative and 0.5 g of Pd/C (10%) in 150 mL of methanol was stirred overnight under H$_2$ (1 atm). After filtering through celite, the solution was concentrated under reduced pressure to give 4.75 mmol of 8.

6.2 Results

Analytical data for exemplary compound of structure 8 are provided below.

6.2.a 4-(6-Aminopyridin-3-yl)-1-benzyl-1,4-diazepan-5-one $^1$H NMR (400 MHz, DMSO-$d_6$) δ 7.70 (d, J=2.4 Hz, 1H), 7.17 (dd, J$_1$=8.8 Hz, J$_2$=2.4 Hz, 1H), 7.30-7.36 (m, 5H), 6.40 (d, J=8.8 Hz, 1H), 5.90 (br s, 2H), 3.66-3.72 (m, 2H), 3.59 (br s, 2H), 2.59-2.71 (m, 6H); MS m/z: 327 (M+1).

Example 7

Preparation of 12

7.1 Halogenation

To a solution of 30.7 mmol of 11 and 5 mL of bromine in 48 mL of hydrobromic acid (48%) at 0° C. was added 24 mL (25 M) of aqueous NaNO$_2$. The mixture was stirred for 1 h at rt before it was neutralized by 145 mL of 3M NaOH. The aqueous solution was extracted with ethyl acetate, and the organic phase was washed with saturated NaCl, dried over MgSO$_4$, and concentrated under a reduced pressure. The crude product was purified by column chromatography to give 24.6 mmol of 12.

7.2 Results

Analytical data for exemplary compounds of structure 12 are provided below.

7.2.a 2-Bromo-5-chloro-pyridine $^1$H NMR (300 MHz, DMSO-d$_6$) δ 8.47 (d, J=2.8 Hz, 1H), 7.89 (dd, J$_1$=8.5 Hz, J$_2$=2.7 Hz, 1H), 7.69 (d, J=8.5 Hz, 1H); MS m/z: 192 (M+1).

7.2.b 2-Bromo-5-(4-fluoro-phenyl)-pyridine $^1$H NMR (300 MHz, DMSO-d$_6$) δ 8.68 (d, J=2.4 Hz, 1H), 8.03 (dd, J$_1$=8.3 Hz, J$_2$=2.6 Hz, 1H), 7.80-7.70 (m, 3H), 7.34 (d, J=6.6 Hz, 1H), 7.32 (d, J=6.8 Hz, 1H); MS m/z: 252 (M+1).

Example 8

Preparation of 14

8.1 Stannylation

To a solution of 17.4 mmol of 13 in 60 mL of dry THF at −78° C. under N$_2$ was added 19.2 mmol of n-BuLi (2.5 M in hexane), and the resulting brown solution was stirred for 30 min before 20.9 mmol of Bu$_3$SnCl was added. The reaction mixture was allowed to warm to room temperature overnight. After the reaction was quenched with saturated NH$_4$Cl and the mixture was extracted with ethyl acetate, the combined organic phase was washed with saturated NaCl, dried over MgSO$_4$, and concentrated under reduced pressure. The crude product was purified by column chromatography on silica gel to give 10.5 mmol of 14.

8.2 Results

Analytical data for exemplary compounds of structure 14 are provided below.

8.2.a 4-Methyl-2-tributylstannanyl-pyridine $^1$H NMR (300 MHz, CDCl$_3$) δ 8.57 (d, J=5.0 Hz, 1H), 7.21 (s, 1H), 6.93 (d, J=4.7 Hz, 1H), 2.29 (s, 3H), 1.61-1.47 (m, 6H), 1.39-1.29 (m, 6H), 1.16-1.08 (m, 6H), 0.87 (t, J=7.3 Hz, 9H); MS m/z: 384 (M+1).

8.2.b 2-Methoxy-6-tributylstannanyl-pyridine $^1$H NMR (300 MHz, CDCl$_3$) δ 7.39 (dd, J$_1$=8.3 Hz, J$_2$=6.9 Hz, 1H), 6.98 (d, J=6.1 Hz, 1H), 6.55 (d, J=8.4 Hz, 1H), 3.93 (s, 3H), 1.62-1.53 (m, 6H), 1.38-1.27 (m, 6H), 1.12-1.05 (m, 6H), 0.89 (t, J=5.9 Hz, 9H); MS m/z: 400 (M+1).

8.2.c 5-Methyl-2-tributylstannanyl-pyridine $^1$H NMR (300 MHz, CDCl$_3$) δ 8.56 (s, 1H), 7.30-7.24 (m, 2H), 2.25 (s, 3H), 1.58-1.44 (m, 6H), 1.36-1.25 (m, 6H), 1.11-1.04 (m, 6H), 0.86 (t, J=7.1 Hz, 9H); MS m/z: 384 (M+1).

8.2.d 4-Pyrrolidin-1-yl-2-tributylstannanyl-pyridine $^1$H NMR (300 MHz, DMSO-d$_6$) δ 8.14 (d, J=4.5 Hz, 1H), 6.68-6.64 (m, 1H), 6.59 (d, J=2.4 Hz, 1H), 3.41 to 3.39 (m, 4H), 1.97 (bs, 4H), 1.58-1.41 (m, 6H), 1.38-1.22 (m, 6H), 1.20-1.00 (m, 6H), 0.83 (t, J=7.3 Hz, 9H); MS m/z: 439 (M+1).

Example 9

Preparation of 16

9.1 General Method: Stille Cross-Coupling

A mixture of 0.3 mmol of 15, 0.36 mmol of 14, and 0.015 mmol of Pd(PPh$_3$)$_4$ in 4 mL of dry toluene was stirred for 2 days at 70° C. under N$_2$. The reaction was quenched with 10 mL of saturated NH$_4$Cl. After the mixture was extracted with EtOAc, the organic phase was washed with saturated NaCl, dried over MgSO$_4$, and concentrated under reduced pressure. The residue was purified by column chromatography on silica gel to give 0.063 mmol of 16.

9.2 Results

Analytical data for an exemplary compound of structure 16 is provided below.

9.2.a 2-Chloro-4-pyridin-2-yl-pyrimidine $^1$H NMR (300 MHz, DMSO-d$_6$) δ 8.79 (d, J=5.0 Hz, 1H), 8.73 (d, J=3.8 Hz, 1H), 8.47 (d, J=8.0 Hz, 1H), 8.36 (d, J=5.2 Hz, 1H), 8.03-7.97 (m, 1H), 7.58-7.53 (m, 1H); MS m/z: 192 (M+1).

Example 10

Preparation of 16

10.1 General Method: Nucleophilic Addition and Oxidation

To a solution of 127 mmol of 14 in 400 mL of dry THF at −78° C. was added 139 mmol of n-butyllithium (2.5 M in hexane) and the solution was stirred for 30 min before 139 mmol of 17 in 100 mL of dry THF was added over a period of 10 min. The resulting mixture was allowed to warm to room temperature with stirring overnight. The reaction was quenched with 10 mL of acetic acid. To the acidic mixture was added 139 mmol of DDQ and the resulting mixture was stirred for 2 days at room temperature before it was quenched with saturated NaHCO$_3$. After the mixture was extracted with ethyl acetate, the organic phase was washed with saturated NaCl, dried over MgSO$_4$, and concentrated in vacuo to afford 62 mmol of 16.

Example 11

Preparation of 18

11.1 General Method

To a solution of 1.34 mmol of 2 or 8 in 20 mL of anhydrous THF was added 2.68 mmol of NaH (60% in mineral oil) and the solution was stirred for 10 min before the addition of 1.34 mmol of 15. The resulting mixture was stirred at reflux for 1 day under N$_2$ and the reaction was quenched with saturated NH$_4$Cl. The reaction mixture was diluted with 100 mL of ethyl acetate and the organic solution was washed with saturated NaCl, dried over MgSO$_4$, and concentrated in vacuo. The crude product was purified by column chromatography on silica gel to afford 0.48 mmol of 18.

11.2 Results

Analytical data for exemplary compounds of structure 18 are provided below.

11.2.a (2-Chloro-pyrimidin-4-yl)-pyridin-2-yl-amine $^1$H NMR (300 MHz, DMSO-d$_6$) δ 10.67 (s, 1H), 8.32 (d, J=6.0 Hz, 2H), 7.83 (d, J=5.5 Hz, 1H), 7.81-7.74 (m, 1H), 7.50 (d, J=8.3 Hz, 1H), 7.07-7.02 (m, 1H); MS m/z: 207 (M+1).

11.2.b (5-Chloro-pyridin-2-yl)-(2-chloro-pyrimidin-4-yl)-amine $^1$H NMR (300 MHz, DMSO-d$_6$) δ 10.83 (s, 1H), 8.35 (d, J=5.8 Hz, 2H), 7.90(dd, J$_1$=2.8 Hz, J$_2$=8.9 Hz, 1H), 7.71 (d, J=5.7 Hz, 1H), 7.60 (d, J=9.1 Hz, 1H); MS m/z: 241 (M+1).

Example 12

Preparation of 19

12.1 General Method: Nucleophilic Replacement

To a solution of 0.58 mmol of 2 or 8 in 20 mL of anhydrous THF was added 1.05 mmol of NaH (60% in mineral oil) and the solution was stirred for 10 min before the addition of 0.53 mmol of 16. The resulting mixture was stirred at reflux for 16 h under N$_2$ and then the reaction was quenched with saturated NH$_4$Cl. The reaction mixture was diluted with 100 mL of ethyl acetate and the organic solution was washed with saturated NaCl, dried over MgSO$_4$, and concentrated in vacuo. The crude product was purified by column chromatography on silica gel to afford a quantitative yield of 19.

12.2 Results

Analytical data for exemplary compounds of structure 19 are provided below.

12.2.a (5-Methoxy-2-pyridin-2-yl-pyrimidin-4-yl)-pyridin-2-yl-amine $^1$H NMR (300 MHz, DMSO-d$_6$) δ 10.75 (bs, 1H), 8.90 (d, J=5.2 Hz, 1H), 8.59-8.48 (m, 3H), 8.40 (t, J=7.8 Hz, 1H), 8.26-8.12 (m, 2H), 7.90 (t, J=6.4 Hz, 1H), 7.44-7.39 (m, 1H), 4.12 (s, 3H); MS m/z: 280 (M+1).

12.2.b (5-Chloro-pyridin-2-yl)-(5-methoxy-2-pyridin-2-yl-pyrimidin-4-yl)-amine.2HCl $^1$H NMR (300 MHz, DMSO-d$_6$) δ 10.10 (s, 1H), 8.86 (d, J=4.7 Hz, 1H), 8.52-8.32 (m, 4H), 8.26 (d, J=8.9 Hz, 1H), 8.06 (dd, J$_1$=8.9 Hz, J$_2$=2.5 Hz, 1H), 7.92-7.87 (m, 1H), 4.09 (s, 3H); MS m/z: 314 (M+1).

12.2.c (5-Methoxy-2-pyridin-2-yl-pyrimidin-4-yl)-(5-pyrrolidin-1-yl-pyridin-2-yl)-amine.2HCl $^1$H NMR (300 MHz, DMSO-d$_6$) δ 10.85 (bs, 1H), 8.89 (d, J=5.0 Hz, 1H), 8.45 (d, J=7.8 Hz, 1H), 8.35 (s, 2H), 7.97 (d, J=9.4 Hz, 1H), 7.91-7.86 (m, 1H), 7.84 (d, J=3.0 Hz, 1H), 7.55 (dd, J$_1$=9.3 Hz, J$_2$=3.0 Hz, 1H), 4.11 (s, 3H), 3.37-3.30 (m, 4H), 1.99 (t, J=6.4 Hz, 4H); MS m/z: 349 (M+1).

12.2.d [5-(3-Fluoro-phenyl)-pyridin-2-yl]-(5-methoxy-2-pyridin-2-yl-pyrimidin-4-yl)-amine.2HCl $^1$H NMR (300 MHz, DMSO-d$_6$) δ 10.55 (bs, 1H), 8.93-8.89 (m, 2H), 8.56 (d, J=7.9 Hz, 1H), 8.46-8.41 (m, 3H), 8.34 (d, J=8.7 Hz, 1H), 7.96-7.91 (m, 1H), 7.71-7.63 (m, 2H), 7.59-7.51 (d, 1H), 7.30-7.22 (m, 1H), 4.12 (s, 3H); MS m/z: 374 (M+1).

12.2.e 1-[6-(5-Methoxy-2-pyridin-2-yl-pyrimidin-4-ylamino)-pyridin-3-yl]-pyrrolidin-2-one 2HCl $^1$H NMR (300 MHz, DMSO-d$_6$) δ 10.27 (bs, 1H), 8.86 (d, J=4.7 Hz, 1H), 8.73 (d, J=2.7 Hz, 1H), 8.45 (d, J=7.8 Hz, 1H), 8.40-8.30 (m, 4H), 7.88-7.83 (m, 1H), 4.10 (s, 3H), 3.90 (t, J=7.0 Hz, 2H), 2.55-2.47 (m, 2H), 2.11 (t, J=7.5 Hz, 2H); MS m/z: 363 (M+1).

12.2f (5-Methoxy-2-pyridin-2-yl-pyrimidin-4-yl)-[5-(4-methyl-piperazin-1-yl)-pyridin-2-yl]-amine.3HCl $^1$H NMR (300 MHz, DMSO-d$_6$) δ 10.67 (bs, 1H), 8.88 (d, J=4.6 Hz, 1H), 8.38 (d, J=7.8 Hz, 1H), 8.31-8.26 (m, 3H), 8.01 (d, J=9.0 Hz, 1H), 7.86-7.78 (m, 2H), 4.10 (s, 3H), 3.94 (d, J=12.7 Hz, 2H), 3.50 (d, J=11.7 Hz, 2H), 3.32-3.14 (m, 4H), 2.79 (d, J=4.5 Hz, 3H); MS m/z: 378 (M+1).

12.2.g (5-Methoxy-2-pyridin-2-yl-pyrimidin-4-yl)-(4-methyl-3,4,5,6-tetrahydro-2H-[1,3']bipyridinyl-6'-yl)-amine.2HCl $^1$H NMR (300 MHz, DMSO-d$_6$) δ 10.59 (bs, 1H), 8.91 (d, J=4.9 Hz, 1H), 8.58-8.44 (m, 3H), 8.43 (s, 1H), 8.25-8.19 (m, 2H), 8.00-7.94 (m, 1H), 4.11 (s, 3H), 3.71 (d, J=11.8 Hz, 2H), 3.16 (bs, 2H), 1.78 (d, J=12.5 Hz, 2H), 1.70-1.45 (m, 3H), 0.95 (d, J=6.1 Hz, 3H); MS m/z: 377 (M+1).

Example 13

Preparation of 20

13.1 Negishi Cross-Coupling

A mixture of 0.08 mmol of 18, 0.08 mmol of 14, and 0.015 mmol of Pd(PPh$_3$)$_4$ in 4 mL of dry THF was stirred at reflux for 2 days under N$_2$. The reaction was quenched with 10 mL of saturated NH$_4$Cl. After the mixture was extracted with EtOAc, the organic phase was washed with saturated NaCl, dried over MgSO$_4$, and concentrated in vacuo. The residue was purified by column chromatography on silica gel to give 0.03 mmol of 20.

13.2 Results

Analytical data for exemplary compounds of structure 20 are provided below.

13.2.a Pyridin-2-yl-(4-pyridin-2-yl-pyrimidin-2-yl)-amine $^1$H NMR (300 MHz, DMSO-d$_6$) δ 9.91 (s, 1H), 8.74 (d, J=3.5 Hz, 1H), 8.69 (d, J=5.1 Hz, 1H), 8.42 (d, J=7.8 Hz, 1H), 8.34 (d, J=8.3 Hz, 1H), 8.30 (d, J=3.6 Hz, 1H), 8.04 (t, J=7.8 Hz, 1H), 7.81 (d, J=4.8 Hz, 2H), 7.59-7.54 (m, 1H), 7.03-6.98 (m, 1H); MS m/z: 250(M+1).

13.2.b (5-Chloro-pyridin-2-yl)-(4-pyridin-2-yl-pyrimidin-2-yl)-amine $^1$H NMR (300 MHz, DMSO-d$_6$) δ 10.24 (s, 1H), 8.76-8.69 (m, 2H), 8.43-8.32 (m, 2H), 8.03 (dd, J$_1$=7.8 Hz, J$_2$=6.0 Hz, 1H), 7.90 (dd, J$_1$=8.9 Hz, J$_2$=2.5 Hz, 1H), 7.86-7.82 (m, 1H), 7.61-7.54 (m, 2H); MS m/z: 284 (M+1).

13.2.c (5-Phenyl-pyridin-2-yl)-(4-pyridin-2-yl-pyrimidin-2-yl)-amine $^1$H NMR (300 MHz, DMSO-d$_6$) δ 10.12 (s, 1H), 8.76-8.71 (m, 2H), 8.64 (d, J=2.5 Hz, 1H), 8.45 (d, J=8.3 Hz, 2H), 8.14 (dd, J$_1$=2.4 Hz, J$_2$=8.7 Hz, 1H), 8.04 (dt, J$_1$=1.8 Hz, J$_2$=7.8

Hz, 1H), 7.82 (d, J=5.0 Hz, 1H), 7.71 (d, J=7.3 Hz, 2H), 7.60-7.55 (m, 1H), 7.50-7.44 (m, 2H), 7.37 (d, J=7.3 Hz, 1H); MS m/z: 326 (M+1).

Example 14

Preparation of 23

14.1 General Method

A mixture of 20.0 mmol of the corresponding carboxylic acid of 22, 15 mL of $SOCl_2$, and 5 drops of DMF was stirred at 60° C. for 3 h. The reaction mixture was concentrated in vacuo. To a solution of the crude 22 in 50 mL of THF was added 20 mmol of 21 and 60 mmol of $Et_3N$ and stirred at room temperature for 2 h. The reaction mixture was concentrated and the residue was diluted with water and AcOEt. The precipitates were collected by filtration and washed with EtOH to give 1.1 mmol of 23.

Example 15

Preparation of 24

15.1 General Method

To a solution of 6.9 mmol of 23 in 20 mL of THF and 20 mL of t-BuOH was added 15 mmol of tBuOK and stirred at 80° C. for 2 h. The reaction mixture was quenched with 3 g of $NH_4Cl$ and extracted with AcOEt. The organic phase was washed with brine, dried over $MgSO_4$, and concentrated in vacuo. The residue was washed with AcOEt-n-hexane (1:2) to give 6.1 mmol of 24.

Example 16

Preparation of 25

16.1 General Method

A mixture of 5.5 mmol of 24 in 15 mL of $POCl_3$ was stirred at 120° C. for 1 h. The reaction mixture was concentrated in vacuo and diluted with AcOEt and $H_2O$, and quenched with $K_2CO_3$. The precipitates were collected by filtration to give 4.7 mmol of 25.

16.2 Results

Analytical data for exemplary compound of structure 25 is provided below.

16.2.a 4-Chloro-2-pyridin-2-ylquinazoline $^1$H NMR (400 MHz, $CDCl_3$) δ 8.79 (d, J=4.9 Hz, 1H), 8.50 (d, J=7.8 Hz, 1H), 8.20 (dd, $J_1$=7.8 Hz, $J_2$=1.0 Hz, 1H), 8.11 (dt, $J_3$=7.8 Hz, $J_2$=1.5 Hz, 1H), 7.83-7.92 (m, 2H), 7.68-7.71 (m, 1H), 7.57-7.61 (m, 1H); MS m/z: 243 (M+1).

Example 17

Preparation of 26

17.1 General Method

To a solution of 1.66 mmol of 25 in 15 mL of DMF was added 5 mmol of 60% NaH in oil at room temperature and 1.66 mmol of 2 or 8, and the resulting mixture was stirred at 60° C. for 4 h. The reaction mixture was concentrated in vacuo and the residue was diluted with water and AcOEt. The mixture was extracted with AcOEt and the organic phase was extracted with diluted HCl. Aqueous phase was made alkaline with $K_2CO_3$ and extracted with AcOEt, and then organic phase was washed with brine, dried over $MgSO_4$, and concentrated. The residue was purified by column chromatography on silica gel to give 0.94 mmol of ca. 1:1 tautomeric mixture of 26.

17.2 General Method

Analytical data for exemplary compound of structure 26 is provided below.

17.2.a N,2-dipyridin-2-ylquinazolin-4-amine and N-[(4Z)-2-pyridin-2-ylquinazolin-4(3H)-ylidene]pyridin-2-amine (ca. 1:1 tautomeric mixture)

$^1$H NMR (400 MHz, DMSO-$d_6$) δ 10.18 (s, 0.5H), 8.72-8.86 (m, 2H), 8.42-8.57 (m, 2.5H), 8.08 (dt, $J_1$=7.8 Hz, $J_2$=2.0 Hz, 0.5H), 7.47-7.98 (m, 6H), 7.32 (d, J=8.3 Hz, 0.5H), 7.11-7.17 (m, 1H); MS m/z: 300 (M+1).

Example 18

Preparation of 29

18.1 General Method

A mixture of 3.0 mmol of 27, 3.0 mmol of 14, and 0.09 mmol of $Pd(PPh_3)_4$ in 20 mL of toluene was stirred at 100° C. for 20 h. The reaction mixture was diluted with AcOEt and $H_2O$, filtrated through celite, and then extracted with AcOEt. The organic phase was washed with brine, dried over $MgSO_4$ and concentrated in vacuo. The residue was purified by column chromatography on silica gel to give 0.46 mmol of 28.

18.2 Results

Analytical data for exemplary compound of structure 28 is provided below.

18.2.a 2-Chloro-4-pyridin-2-ylquinazoline $^1$H NMR (300 MHz, $CDCl_3$) δ 8.95-8.99 (m, 1H), 8.83-8.86 (m, 1H), 8.27 (dt, $J_1$=7.9 Hz, $J_2$=0.9 Hz, 1H), 7.92-8.07 (m, 3H), 7.65-7.71 (m, 1H), 7.49-7.54 (m, 1H); MS m/z: 243 (M+1).

18.3 General Method

To a solution of 1.66 mmol of 28 in 15 mL of DMF was added 5 mmol of 60% NaH in oil at room temperature and 1.66 mmol of 2 or 8, and the resulting mixture was stirred at 60° C. for 4 h. The reaction mixture was concentrated in vacuo and the residue was diluted with water and AcOEt. The mixture was extracted with AcOEt and the organic phase was extracted with diluted HCl. Aqueous phase was made alkaline with $K_2CO_3$ and extracted with AcOEt, and then organic phase was washed with brine, dried over $MgSO_4$, and concentrated. The residue was purified by column chromatography on silica gel to give 0.90 mmol of 29.

18.4 Results

Analytical data for exemplary compound of structure 29 is provided below.

18.4.a N,4-Dipyridin-2-ylquinazolin-2-amine $^1$H NMR (400 MHz, DMSO-$d_6$) δ 10.03 (s, 1H), 8.84 (d, J=5.4 Hz, 1H), 8.64 (d, J=7.8 Hz, 1H), 8.60 (d, J=8.3 Hz, 1H), 8.34 (d, J=4.9 Hz, 1H), 8.21 (d, J=7.8 Hz, 1H), 8.11 (dt, $J_1$=7.4 Hz, $J_2$=1.5 Hz, 1H), 7.82-7.90 (m, 3H), 7.64-7.67 (m, 1H), 7.44 (t, J=7.8 Hz, 1H), 7.02-7.06 (m, 1H); MS m/z: 300 (M+1).

Example 19

Preparation of the Metal Complex 30

19.1 Synthesis 0.1 mL of 1.0 M $FeClO_4$ in ether is added to a solution of 0.2 mmol of 20 in EtOH at 60° C. A white precipitate forms immediately. To this mixture is added 0.06 mL of triethyl amine and the resulting mixture is stirred for 20 min. After the mixture is cooled to rt, the white precipitate is filtered to yield 30.

Example 20

20.1 Assay for Compound Activity Towards hSK Channels

Cells expressing small conductance, calcium activated potassium channels, such as SK-like channels were loaded with $^{86}Rb^+$ by culture in media containing $^{86}RbCl$. Following loading, the culture media was removed and the cells were washed in EBSS to remove residual traces of $^{86}Rb^+$. Cells were preincubated with the drug (0.01 to 30 µM in EBSS) and then $^{86}Rb^+$ efflux was stimulated by exposing cells to EBSS solution supplemented with a calcium ionophore, such as ionomycin, in the continued presence of the drug. After a suitable efflux period, the EBSS/ionophore solution was removed from the cells and the $^{86}Rb^+$ content was determined by Cherenkov counting (Wallac Trilux). Cells were then lysed with a SDS solution and the $^{86}Rb^+$ content of the lysate was determined. Percent $^{86}Rb^+$ efflux was calculated according to the following equation:

$$(^{86}Rb^+ \text{ content in } EBSS/(^{86}Rb^+ \text{ content in } EBSS + {}^{86}Rb^+ \text{ content of the lysate})) \times 100$$

20.2 Results

Compounds tested in this assay, along with their hSK2 inhibitory activity, are provided in Table 1.

TABLE 1

| Compound Name | hSK2 Inhibitory Activity |
|---|---|
| (4-Methyl-pyridin-2-yl)-(4-pyridin-2-yl-pyrimidin-2-yl)-amine | ++++ |
| $N^2$-(5-Methoxy-2-pyridin-2-yl-pyrimidin-4-yl)-pyridine-2,5-diamine | ++++ |
| (5-Methoxy-2-pyridin-2-yl-pyrimidin-4-yl)-(5-pyrrolidin-1-yl-pyridin-2-yl)-amine | ++++ |
| 1-[6-(5-Methoxy-2-pyridin-2-yl-pyrimidin-4-ylamino)-pyridin-3-yl]-pyrrolidin-2-one | ++++ |
| (5-Methoxy-2-pyridin-2-yl-pyrimidin-4-yl)-(5-thiophen-2-yl-pyridin-2-yl)-amine | ++++ |
| (5-Methoxy-2-pyridin-2-yl-pyrimidin-4-yl)-(4-methyl-3,4,5,6-tetrahydro-2H-[1,3']bipyridinyl-6'-yl)-amine | ++++ |
| (5-Methoxy-pyridin-2-yl)-(5-methoxy-2-pyridin-2-yl-pyrimidin-4-yl)-amine | ++++ |
| (5-Methoxy-2-pyridin-2-yl-pyrimidin-4-yl)-(5-thiophen-3-yl-pyridin-2-yl)-amine | ++++ |
| Pyridin-2-yl-(4-pyridin-2-yl-pyrimidin-2-yl)-amine | ++++ |
| (5-Methoxy-2-pyridin-2-yl-pyrimidin-4-yl)-(4-methyl-pyridin-2-yl)-amine | ++++ |
| (5-Methoxy-2-pyridin-2-yl-pyrimidin-4-yl)-pyridin-2-yl-amine | +++ |
| (5-Chloro-pyridin-2-yl)-(5-methoxy-2-pyridin-2-yl-pyrimidin-4-yl)-amine | +++ |
| (5-Chloro-pyridin-2-yl)-(4-pyridin-2-yl-pyrimidin-2-yl)-amine | +++ |
| $N^2$-(5-Methoxy-2-pyridin-2-yl-pyrimidin-4-yl)-N5,N5-dimethyl-pyridine-2,5-diamine | +++ |
| (5-Methoxy-2-pyridin-2-yl-pyrimidin-4-yl)-(5-phenyl-pyridin-2-yl)-amine | +++ |
| (5-Phenyl-pyridin-2-yl)-(4-pyridin-2-yl-pyrimidin-2-yl)-amine | +++ |
| (5-Methoxy-2-pyridin-2-yl-pyrimidin-4-yl)-[5-(4-methyl-piperazin-1-yl)-pyridin-2-yl]-amine | +++ |
| (5-Methoxy-2-pyridin-2-yl-pyrimidin-4-yl)-[5-(5-methyl-furan-2-yl)-pyridin-2-yl]-amine | +++ |
| [5-(3-Fluoro-phenyl)-pyridin-2-yl]-(5-methoxy-2-pyridin-2-yl-pyrimidin-4-yl)-amine | +++ |
| (5-Fluoro-pyridin-2-yl)-(5-methoxy-2-pyridin-2-yl-pyrimidin-4-yl)-amine | +++ |
| Pyridin-2-yl-(2-pyridin-2-yl-quinazolin-4-yl)-amine | +++ |
| 4-Chloro-2,6-di-pyridin-2-yl-pyrimidine | ++ |
| [2-(6-methyl-pyridin-2-yl)-pyrimidin-4-yl]-pyridin-2-yl-amine | ++ |
| (5-Chloro-pyridin-2-yl)-(2-pyridin-2-yl-pyrimidin-4-yl)-amine | ++ |
| [4-(6-methyl-pyridin-2-yl)-pyrimidin-2-yl]-pyridin-2-yl-amine | ++ |
| (6-methyl-2-pyridin-2-yl-pyrimidin-4-yl)-pyridin-2-yl-amine | + |
| (5-Methoxy-2-pyridin-2-yl-pyrimidin-4-yl)-(5-nitro-pyridin-2-yl)-amine | + |
| (4-Pyridin-2-yl-pyrimidin-2-yl)-(5-trifluoromethyl-pyridin-2-yl)-amine | + |
| N-(5-Methoxy-2-pyridin-2-yl-pyrimidin-4-yl)-N'-pyridin-2-yl-hydrazine | + |
| (5-Bromo-pyridin-2-yl)-(5-methoxy-2-pyridin-2-yl-pyrimidin-4-yl)-amine | + |
| Methyl-pyridin-2-yl-(4-pyridin-2-yl-pyrimidin-2-yl)-amine | + |
| Pyridin-2-yl-(4-pyridin-2-yl-quinazolin-2-yl)-amine | + |
| (5-Methoxy-2-pyridin-2-yl-pyrimidin-4-yl)-(5-trifluoromethyl-pyridin-2-yl)-amine | + |
| (5-Chloro-6-methyl-2-pyridin-2-yl-pyrimidin-4-yl)-(5-trifluoromethyl-pyridin-2-yl)-amine | + |
| (2,6-Di-pyridin-2-yl-pyrimidin-4-yl)-pyridin-2-yl-amine | + |
| (2,6-Di-pyridin-2-yl-pyrimidin-4-yl)-(5-trifluoromethyl-pyridin-2-yl)-amine | + |

Key:
+ indicates 30 µM > IC50 > 5.0 µM;
++ indicates 5.0 µM > IC50 > 1.0 µM;
+++ indicates 1.0 µM > IC50 > 0.1 µM;
++++ indicates 0.1 µM > IC50 > 0.0 µM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to Formula I:

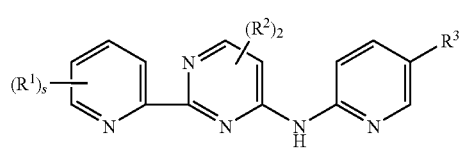

(I)

or a pharmaceutically acceptable salt thereof,
wherein
s is an integer from 1 to 4;
$R^1$ is H, —OH, —NO$_2$, —SO$_2$NH$_2$, halogen, substituted or unsubstituted alkyl, substituted or unsubstituted heteroalkyl, substituted or unsubstituted 3- to 7- membered cycloalkyl, substituted or unsubstituted 5- to 7- membered heterocycloalkyl, substituted or unsubstituted aryl, substituted or unsubstituted heteroaryl, or —NR$^7$R$^8$, wherein R$^7$ and R$^8$ are independently H, halogen, substituted or unsubstituted alkyl, substituted or unsubstituted heteroalkyl, substituted or unsubstituted 5- to 7- membered cycloalkyl, substituted or unsubstituted 5- to 7- membered heterocycloalkyl, substituted or unsubstituted aryl, or substituted or unsubstituted heteroaryl, wherein R$^7$ and R$^8$ are optionally joined together with the nitrogen to which they are attached to form a substituted or unsubstituted 5- to 7- membered heterocycloalkyl, or substituted or unsubstituted heteroaryl;
each R$^2$ is independently —H or —OCH$_3$; and
R$^3$ is H, —NH$_2$, —NO$_2$, halogen, substituted or unsubstituted alkyl, substituted or unsubstituted heteroalkyl, substituted or unsubstituted 3- to 7- membered cycloalkyl, substituted or unsubstituted 5- to 7- membered heterocycloalkyl, substituted or unsubstituted aryl, or substituted or unsubstituted heteroaryl;
wherein two R$^3$ groups are optionally joined together with the atoms to which they are attached to form a substituted or unsubstituted ring.

2. The compound of claim 1, wherein
R$^1$ is H, substituted or unsubstituted alkyl, substituted or unsubstituted heteroalkyl, or substituted or unsubstituted aryl; and
R$^3$ is H, —NH$_2$, —NO$_2$, halogen, substituted or unsubstituted alkyl, substituted or unsubstituted heteroalkyl, substituted or unsubstituted aryl, or substituted or unsubstituted heteroaryl.

3. The compound of claim 2, wherein
R$^1$ is H, methyl, —NH$_2$, or unsubstituted phenyl;
R$^2$ is H, or —OCH$_3$; and
R$^3$ is H, —NH$_2$, —NO$_2$, Cl, Br, F, methyl, phenyl, fluorophenyl, —CF$_3$, —OCH$_3$, dimethylamino, unsubstituted piperidine, p-methyl morpholino, unsubstituted pyrrolidinonyl, unsubstituted 2-thiophenyl, unsubstituted 3-thiophenyl, unsubstituted furanyl, or n-methyl piperizinyl.

4. The compound of claim 1, wherein R$^3$ is Cl or —NR$^7$R$^8$, wherein R$^7$ and R$^8$ are independently H, halogen, substituted or unsubstituted alkyl, substituted or unsubstituted heteroalkyl, substituted or unsubstituted 5- to 7-membered cycloalkyl, substituted or unsubstituted 5- to 7-membered heterocycloalkyl, substituted or unsubstituted aryl, or substituted or unsubstituted heteroaryl, wherein R$^7$ and R$^8$ are optionally joined together with the nitrogen to which they are attached to form a substituted or unsubstituted 5- to 7-membered heterocycloalkyl, or substituted or unsubstituted heteroaryl.

5. The compound of claim 4, wherein R$^3$ is Cl, —NH$_2$, —N(CH$_3$)$_2$,

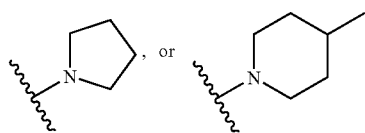

, or

.

6. A metal complex, comprising a polyvalent metal ion and a polydentate component of a metal ion chelator, wherein said polydentate component is a compound according to claim 1.

7. The complex of claim 6, wherein said polyvalent metal ion is selected from iron, zinc, copper, cobalt, manganese, and nickel.

8. A method of treating a disorder or condition through modulation of a potassium ion channel, said method comprising administering to a subject in need of such treatment, an effective amount of an SK channel modulatory compound of claim 1, wherein the disease is selected from the group consisting of epilepsy, seizures, learning and memory deficits, mood disorders, Parkinson's disease, and psychotic disorders.

9. A pharmaceutical composition comprising a pharmaceutically acceptable carrier and a compound of the compound of claim 1.

10. The compound of claim 3, wherein R$^1$ is —H, (R$^2$)$_2$ are —H and —OCH$_3$, and R$^3$ is —Cl.

11. The compound of claim 10, wherein the compound is selected from the group consisting of:
(5-Methoxy-2-pyridin-2-yl-pyrimidin-4-yl)-(5-pyrrolidin-1-yl-pyridin-2-yl)-amine,
(5-Methoxy-2-pyridin-2-yl-pyrimidin-4-yl)-(5-thiophen-2-yl-pyridin-2-yl)-amine,
(5-Methoxy-2-pyridin-2-yl-pyrimidin-4-yl)-(4-methyl-3,4,5,6-tetrahydro-2H-[1,3']bipyridinyl-6'-yl)-amine,
(5-Methoxy-pyridin-2-yl)-(5-methoxy-2-pyridin-2-yl-pyrimidin-4-yl)-amine,
(5-Methoxy-2-pyridin-2-yl-pyrimidin-4-yl)-(5-thiophen-3-yl-pyridin-2-yl)-amine,
(5-Methoxy-2-pyridin-2-yl-pyrimidin-4-yl)-pyridin-2-yl-amine,
(5-Chloro-pyridin-2-yl)-(5-methoxy-2-pyridin-2-yl-pyrimidin-4-yl)-amine,
N$^2$-(5-Methoxy-2-pyridin-2-yl-pyrimidin-4-yl)-N5,N5-dimethyl-pyridine-2,5-diamine,
(5-Methoxy-2-pyridin-2-yl-pyrimidin-4-yl)-(5-phenyl-pyridin-2-yl)-amine,
(5-Methoxy-2-pyridin-2-yl-pyrimidin-4-yl)-[5-(4-methyl-piperazin-1-yl)-pyridin-2-yl]-amine,
(5-Methoxy-2-pyridin-2-yl-pyrimidin-4-yl)-[5-(5-methyl-furan-2-yl)-pyridin-2-yl]-amine,
[5-(3-Fluoro-phenyl)-pyridin-2-yl]-(5-methoxy-2-pyridin-2-yl-pyrimidin-4-yl)-amine, (5-Fluoro-pyridin-2-yl)-(5-methoxy-2-pyridin-2-yl-pyrimidin-4-yl)-amine,

[2-(6-Methyl-pyridin-2-yl)-pyrimidin-4-yl]-pyridin-2-yl-amine, (5-Chloro-pyridin-2-yl)-(2-pyridin-2-yl-pyrimidin-4-yl)-amine, (6-Methyl-2-pyridin-2-yl-pyrimidin-4-yl)-pyridin-2-yl-amine, (5-Methoxy-2-pyridin-2-yl-pyrimidin-4-yl)-(5-nitro-pyridin-2-yl)-amine, (5-Bromo-pyridin-2-yl)-(5-methoxy-2-pyridin-2-yl-pyrimidin-4-yl)-amine, (5-Methoxy-2-pyridin-2-yl-pyrimidin-4-yl)-(5-trifluoromethyl-pyridin-2-yl)-amine and (5-Chloro-6-methyl-2-pyridin-2-yl-pyrimidin-4-yl)-(5-trifluoromethyl-pyridin-2-yl)-amine.

12. A pharmaceutical composition comprising a pharmaceutically acceptable carrier and a compound of the compound of claim 11.

13. A method of treating a disease through modulation of a potassium ion channel, said method comprising administering to a subject in need of such treatment, an effective amount of a SK channel modulatory compound of claim 11, wherein the disease is selected from the group consisting of epilepsy, seizures, learning and memory deficits, mood disorders, Parkinson's disease, and psychotic disorders.

14. A pharmaceutical composition comprising a pharmaceutically acceptable carrier and a compound of the compound of claim 10.

15. A method for treating a disease through modulation of a potassium ion channel, said method comprising administering to a subject in need of such treatment, an effective amount of a SK channel modulatory compound of claim 10, wherein the disease is selected from the group consisting of epilepsy, seizures, learning and memory deficits, mood disorders, Parkinson's disease, and psychotic disorders.

* * * * *